United States Patent
Varshneya et al.

(10) Patent No.: US 6,816,266 B2
(45) Date of Patent: *Nov. 9, 2004

(54) FIBER OPTIC INTERFEROMETRIC VITAL SIGN MONITOR FOR USE IN MAGNETIC RESONANCE IMAGING, CONFINED CARE FACILITIES AND IN-HOSPITAL

(75) Inventors: Deepak Varshneya, 3057 Caminito Sagunto, Del Mar, CA (US) 92104-3934; John L. Maida, Jr., Houston, TX (US); Larry A. Jeffers, Minerva, OH (US)

(73) Assignee: Deepak Varshneya, Del Mar, CA (US)

( * ) Notice: Subject to any disclaimer, the term of this patent is extended or adjusted under 35 U.S.C. 154(b) by 23 days.

This patent is subject to a terminal disclaimer.

(21) Appl. No.: 10/299,414

(22) Filed: Nov. 19, 2002

(65) Prior Publication Data

US 2003/0095263 A1 May 22, 2003

Related U.S. Application Data

(63) Continuation-in-part of application No. 09/499,889, filed on Feb. 8, 2000, now Pat. No. 6,498,652.

(51) Int. Cl.[7] ................................................ G01B 9/02
(52) U.S. Cl. ....................................................... 356/477
(58) Field of Search ................................ 356/477, 478, 356/479, 481, 483; 250/227.19, 227.27

(56) References Cited

U.S. PATENT DOCUMENTS 5,212,379 A    5/1993   Nafarrate et al.

(List continued on next page.)

OTHER PUBLICATIONS

Invivo Research, Inc., Questions & Answers from the JCAHO, Conscious Sedations (Questions about the Anesthesia Continuun by Ann Kobs, www.invivoresearch.com/topics/vital_signs/jcaho.html.

(List continued on next page.)

Primary Examiner—Samuel A. Turner
Assistant Examiner—Patrick Connolly
(74) Attorney, Agent, or Firm—Pearne & Gordon LLP

(57) ABSTRACT

A fiber optic monitor that utilizes optical phase interferometry to monitor a patient's vital signs such as respiration, cardiac activity, blood pressure and body's physical movement. The monitor, which is non-invasive, comprises an optical fiber interferometer that includes an optical fiber proximately situated to the patient so that time varying acousto-mechanical signals from the patient are coupled into the optical fiber. Responsive thereto, the interferometer generates a time-varying optical intensity resulting from the interference of optical signals, which are detected at a photo-detector. A signal processor coupled to the optical detector provides one or more processed output signals indicative of the vital functions. The monitor system has broad applicability, from routine monitoring of infants at home to detection of apnea, arrhythmia, blood pressure and trauma. The system can be implemented in embodiments ranging from a low cost in-home monitor for infants to a high end product for in hospital use. The monitor can be integrated with other sensors such as an EKG, a video or still camera, an oxygen sensor, a carbon dioxide sensor, temperature sensor or a microphone to get additional required information depending on the application. When integrated and combined with EKG information, the monitor provides ballisto-mechanical information of the heart for early diagnosis of cardiac conditions or prediction of events or for correcting corrupted EKG signals due to time varying magnetic and electric fields. In some embodiments of the monitor, the system can be made portable so that the patient can walk around while still being continuously monitored for vital signs. Another suitable design measures blood pressure continuously and non-invasively by containing the fiber optic sensor in a cuff that wraps around an arterial wall of the patient. The fiber optic monitor may be designed for use in a variety of settings including an operating room, a recovery room, an intensive care unit, a magnetic resonance imaging laboratory, a computerized tomography scan laboratory and an elderly care facility.

45 Claims, 14 Drawing Sheets

U.S. PATENT DOCUMENTS

| | | |
|---|---|---|
| 5,241,300 A | 8/1993 | Buschmann |
| 5,291,013 A | 3/1994 | Nafarrate et al. |
| 6,498,652 B1 * | 12/2002 | Varshneya et al. .......... 356/477 |

OTHER PUBLICATIONS

Invivo Researach, Inc., Pulse Oximeter's Reliability in detecting Hypoxemia and Bradycardia: Comparision between Nellcor N–200, N–3000 and Masimo SET®, www.invivoresearch.com/topics/vital_signs/reliability.html.

Useful Life of Pulse Oximeter Sensors in a NICU, T.A. Holmes et al., www.invivoresearch.com/topics/vital_signs/sensor_life.html.

Invivo Research, Inc., Advances in ECG Filtering Process for Patient Monitoring and Cardic Gating in MRI F.G. Shellock, www.invivoresearch.com/topics/vital_signs/moon.html.

Several States Now Mandate Stringent Criteria for Physiolocigal Monitoring of Anesthetized Patents, M. Schiebler, etal. www.invivoresearch.com/topics/vital_signs/survey.html.

Monitoring Patients During MR Procedures: A Review, F.G. Shellock et al., www.invivoresearch.com/topics/vital_signs/review.html.

Nornal Sinus Rhythm(NSR), www.rchc.rush.edu/rmawebfiles/abnl%20rhythm%20for%20parents%20body.htm.

Anesthesia in the MRI Suite, hhtp://www.gasnet.org/mri/introduction_br.php.

Anesthesia Equipment in the MRI Suite, Charlotte Bell, MD and Rebecca Dubowy, MD, Department of Anesthesiology, Yale University School of Medicine, New Haven, CT, USA. www.gasnet.org/mri/about/about–mri1_br.php.

Anesthesia Equipment in the MRI Suite, The Process of Magnetic Resonance Imaging, Charlotte Bell, MD et al. www.gasnet.org/mri/about/about–mri2_br.php.

Anesthesia Equipment in the MRI Suite, Monitoring in the MRI Suite, Charlotte Bell, MD et al., www.gasnet.org/mri/about/about–mri3_br.php.

MRI Patient Vital Signs Monitoring System, Product Description, www.gasnet.org/mri/equipment/invivo_br.php.

Optovent™ RR 9700, Respiratory rate and Apnea Monitor, Product Description, www.gasnet.org/mri/equipment/optovent_br.php.

Datex–Ohmeda Aestive™/5 MRI Anesthesia System, www.gasnet/org/mri/equipment/datex–ohmeda_br.php.

Drager, Narcomed MRI, Titus, PM 8050 MRI, www.gasnet.org/mri/equipment/draeger1_br.php.

Drager, Titus, Narkomed MRI, PM 8050MI, Basic Unit, www.gasnet.org/mri/equipment/draeger2_br.php.

Drager, Narkomed MRI Titus, PM8050 MRI, Ambient conditions, www.gasnet.org/mri/equipment/draeger3_br.php.

Anesthesia in the MRI Suite, biblipgraphy of suitable monitors and equipment, www.gasnet.org/mri/biblipgraphy/bibliography1_br.php.

Anesthesia in the MRI Suite, bibliography of sedation/anesthesia techniques www.gasnet.org/mri/bibliography/bibliography2_br.php.

Using Anesthesia Information Systems to Optimize Afternoon and Evening Anesthesia Staffing, F. Dexter, M.D., PhD. Introduction, www.gasnet.org/mri/aims/dexter1_br.php.

Using Anesthesia Information Systems to Optimize Afternoon and Evening Anesthesia Staffing, F. Dexter, M.D., PhD. References, www.gasnet.org/mri/aims/dexter5_br.php.

Using Anesthesia Information Systems to Optimize Afternoon and Evening Anesthesia Staffing, F. Dexter, M.D., PhD. Second–shift staffing algorithm, www.gasnet.org/aims/dexter2_br.php.

Using Anesthesia Information Systems to Optimize Afternoon and Evening Anesthesia Staffing, F. Dexter, M.D., PhD. Experience in using the algorithm, www.gasnet.org/aims/dexter3_br.php.

Using Anesthesia Information Systems to Optimize Afternoon and Evening Anesthesia Staffing, F. Dexter, M.D., PhD. Conclusionss, www.gasnet.org/aims/dexter4_br.php.

Advantages and Pitfalls of Perioperative Electronic Records, G.L. Gibby MD, Introduction,. www.gasnet.org/aims/gibby1_br.php.

Advantages and Pitfalls of Perioperative Electronic Records, G.L. Gibby MD, Moving Patients through the system, www.gasnet.org/aims/gibby2_br.php.

Advantages and Pitfalls of Perioperative Electronic Records, G.L. gibby MD, They work in our experience, www.gasnet.org/aims/gibby3_br.php.

Advantages and Pitfalls of Perioperative Perioperative Electronic Records, G.L. Gibby MD, Multiple input mechanisms a must, www.gasnet.org/aims/gibby4_br.php.

Advantages and Pitfalls of Perioperative Electronic Records, G.L. Gibby MD, Conclusion, www.gasnet.org/aims/gibby5_br.php.

Advantages and Pitfalls of Perioperative Electronic Records, G.L. Gibby MD, References, www.gasnet.org/aims/gibby6_br.php.

Anesthesia Information Systems and Perioperative Work Flow, Michael O'Reilly, MD., Introduction www.gasnet.org/aims/oreilly1_br.php.

Anesthesia Information Systems and Perioperative Work Flow, Michael O'Reilly, MD., What is an Anesthesia Information System?, www.gasnet.org/aims/oreilly2_br.php.

Anesthesia Information Systems and Perioperative Work Flow, Michael O'Reilly, MD., Moving patients through the system, www.gasnet.org/aims/oreilly3_br.php.

Anesthesia Information Systems and Perioperative Work Flow, Michael O'Reilly, MD., Does the patient need to be seen in advance of surgery?, www.gasnet.org/aims/oreilly4_br.php.

Anesthesia Information Systems and Perioperative Work Flow, Michael O'Reilly, MD., Is the patient medically ready to go to the OR?, www.gasnet.org/aims/oreilly5_br.php.

Anesthesia Information Systems and Perioperative Work Flow, Michael O'Reilly, MD., Is there a practice guideline for this procedure? www.gasnet.org/aims/oreilly6_br.php.

Anesthesia Information Systems and Perioperative Work Flow, Michael O'Reilly, MD., We are the co–morbidity and phenotype doctors? Conclusions, www.gasnet.org/aims/oreilly7_br.php.

Anesthesia Information Systems and Perioperative Work Flow, Michael O'Reilly, MD., References, www.gasnet.org/aims/oreilly8_br.php.

Deio specializes in clinical Information Systems (CIS), www.gasnet.org/aims/datex_br.php.

DucuSys Anesthesia Information System, Product Description, www.gasnet.org/aims/docsys_br.php.

Drager Medical Saturn Information System, Product Description, www.gasnet.org/aim/draeger_br.php.

GE Medical Systems, Centricity™ Perioperative Anesthesia, Product Description, www.gasnet.org/aims/gemidical_br.php.

GASNet Video Library, www.gasnet.org/videos/index_br.php.

Anesthesiologist's Manual of Surgical Procedures, Richard A. Jaffe et al., Raven Press, 1994 Reviewed by A B. Hilton, MD, www.gasnet.org/review/articles/surgical-procedures_br.php.

Clinical Transesophageal Echocardiography: A Problem-Oriented Approach, Yasu Oka et al., 1996, www.gasnet.org/reviews/article/tee_br.php.

Review: Death on Request, M. Nedorhorst, www.gasnet.org/reviews/articles/death_br.php.

Book Review: Drug Infusions in Anesthesiology, 2nd Edition, R.J. Fragen, ed., Lippincott–Raven, 1996, Reviewed by A.M. De Wolfe, MD, www.gasnet.org/reviews/articles/drug-infusions_br.php.

Genetics in Anesthesiology—Syndromes and Science, Guy L. Weinberg, Butterworth–Heinemann, Reviewed by G.B. Russell, MD., mwww.gasnet.org/reviews/article/weinberg_br.php.

Book Review: Handbook of Pharmacology and Physiology in Anesthetic Practice, Robert K. Stoelting, Lippincott–Raven Press, 1995, www.gasnet.org/reviews/articles/stoelting_br.php.

Book Review: The Art of Serial Communication, RWD Nickalls et al., www.gasnet.org/reviews/articles/sercom_br.php.

Book Review: With Numb toes and Arching soles: Coping with Peripheal Neuropathy, Reviewed by Shu–Ming Wang www.gasnet.org/reviews/article/numbtoes_br.php.

Book Review: Practical Anaesthesia and Analgesia for Day Surgery, J.M. Millar et al., Reviewed by Kathryn King MD., www.gasnet.org/reviews/articles/pracanesanalg_br.php.

The Anesthesia Gas Machine, Vaporizers, Compressed Gases, Safety: Avoiding the Pitfalls, Michael P. Dosch, www.gasnet.org/machine/part1.htm.

Invivo Research, The Agent Revolutions, Articles & Clinical Information www.inivoresearch.com/topics/vital_signs/agent.html.

"Phonocardiography: Measurement of Heart Sounds", www.seas.smu.edu/~cd/EE5340/lect20/tsld011.htm.

"Normal Sinus Rhythm", www.rchc.rush.edu/rmawebfiles/abnl%20rhythm%20for%20parents%20body.htm and www.rchc.rush.edu/rmawebfiles/EKG%20for%20parents%20body.htm.

EE5340 Introduction to Biomedical Engineering–Lexture Slives: 368–386, http://engr.smu.edu/~cd/EE5340/lect20/sld001.htm through http://engr.smu.edu/~cd/EE5340/lect20/sld0201.htm.

Catheters and Guide Wires In Interventional MRI: Problems and Solutions, M.K. Konings et al. Medica Mundi, 45/1 Mar. 2001.

Ameerican College of Radiology White Paper on MR Safety, Charlotte Bell, MD et al., AJR 2002; 178:1335–1347.

* cited by examiner

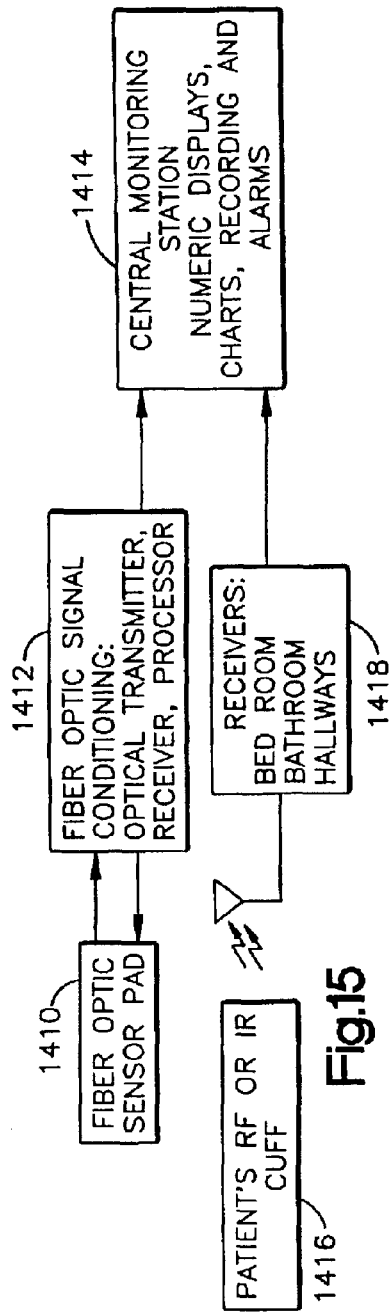
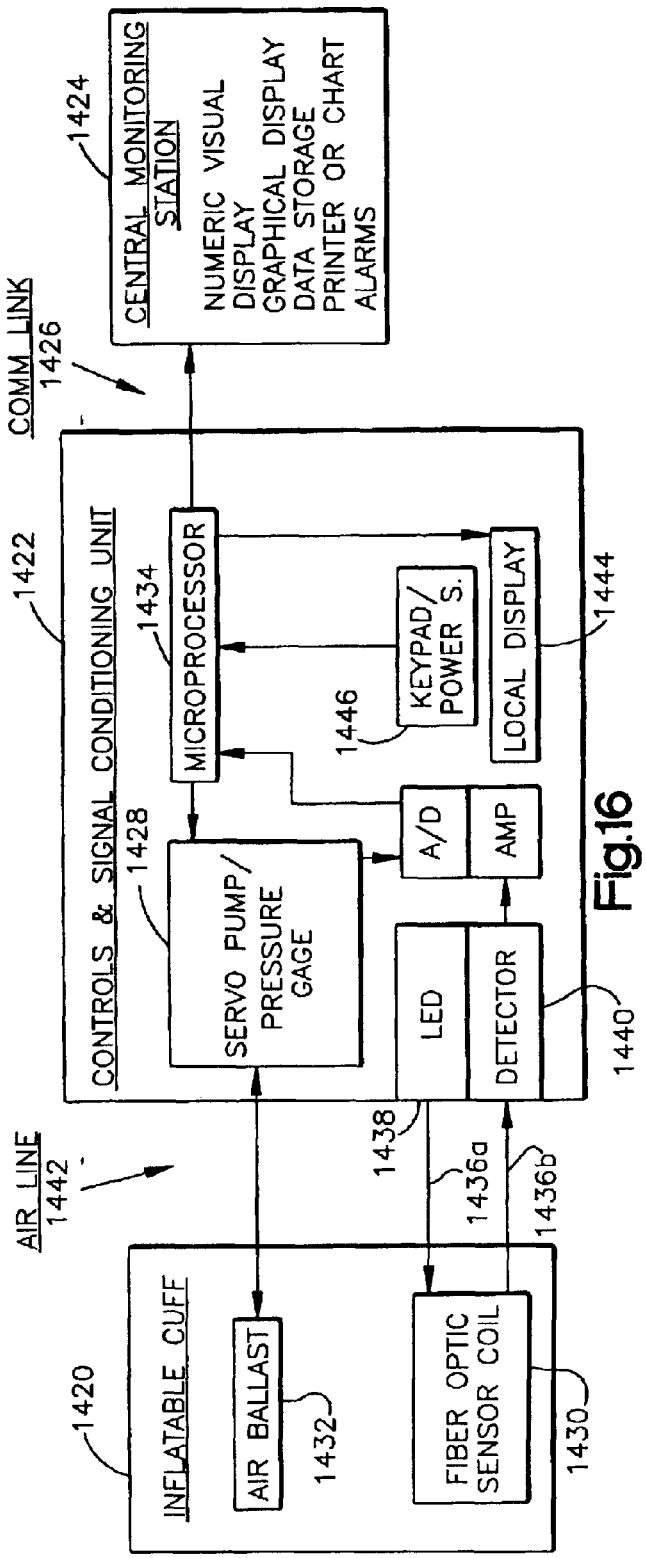

FIBER OPTIC INTERFEROMETRIC VITAL SIGN MONITOR FOR USE IN MAGNETIC RESONANCE IMAGING, CONFINED CARE FACILITIES AND IN-HOSPITAL

CROSS-REFERENCE TO RELATED APPLICATION

This is a continuation-in-part of patent application Ser. No. 09/499,889 entitled, "Fiber Optic Monitor Using Interferometry for Detecting Vital Signs of a Patient," filed on Feb. 8, 2000 now U.S. Pat. No. 6,498,652, which is incorporated herein by reference in its entirety.

FIELD OF THE INVENTION

The present invention generally relates to vital sign monitors for detecting physiological parameters such as heartbeat, respiration, physical movement, blood pressure and other bodily activities of a patient for use in a magnetic resonance imaging (MRI) environment, confined care facilities (e.g., geriatrics) and in-hospital during surgery, postoperative recovery and intensive care units.

DESCRIPTION OF RELATED ART

1. Background of Vital Sign Monitoring in Magnetic Resonance Imaging Labs

Use of Magnetic Resonance Imaging (MRI) is rapidly growing in the U.S. and other parts of the world for investigations and diagnosis of many diseases. Statistical data published by In-vivo Research shows that over 18 million scans are performed per year in the U.S. alone. To better understand the problems of monitoring patients undergoing MRI scanning, a summary of the key steps required in generating a patient's image is provided:

1. A strong magnetic field, on the order of 1.5 to 2 Teslas (1 Tesla=10,000 Gauss, earth's magnetic field is 1 Gauss), is required to align all randomly oriented nuclei cells of the patient;

2. Radio frequency (RF) pulses, directed at the patient, are used in the presence of the external magnetic field, to cause the cell nuclei to absorb more energy producing magnetic resonance. This is generally referred to as super charging of the nuclei, which further changes their alignment from the original state;

3. The RF supercharged cell nuclei recover their original state of alignment within the magnetic field by re-emitting the absorbed RF energy. The RF signal re-emitted by each tissue is proportional to the difference between the energized magnetic resonance states and the original alignment states. Tissue imaging contrast develops as a result of the different rates of realignment;

4. Time varied magnetic field (TVMF) gradients are applied briefly to spatially encode the RF signals emitted from the patient tissues;

5. The RF coils in the MRI pick up these spatially encoded RF signals emitted from the tissues and are transformed by a computer into 2 or 3 dimensional images.

The strong magnetic field, RF pulses and/or TVMF gradients are referred to in this disclosure as "the MRI environment."

Of the 18 million MRI scans done per year, approximately 10% of the patients are sedated during scanning for a variety of reasons. These patients are sedated using general, conscious intravenous (IV, spinal and epidural), orally administered (chewing tablets) or local anesthesia. If anesthesia is administered during MRI scanning, the law generally mandates that the patient's vital signs be monitored continuously. Monitoring of different vital parameters depends on the patient condition such as heart patient, pediatric or claustrophobic and the type of anesthesia administered. In the past, the attending anesthesiologist made the decision. More recently, the American Society for Anesthesia has published guidelines describing both the physiological monitoring equipment and parameters that must be measured for different patient types ("Both sedated and critically III require Monitoring during MRI", Mark Schiebler, MD, et al. www.invivoresearch.com/topics/vital signs/survey.html) and White Paper on "MRI Safety", Charlotte Bell, MD, et al., American College of Radiology, *AJR* 2002; 178:1335–1347). According to these guidelines, the key parameters that must be continuously monitored include: EKG, Pulse Oximetry, Blood pressure, and Respiration by end tidal $CO_2$/Capnograph or other methods.

Generally the three broad categories of problems are experienced when monitoring the vital signs of sedated patients in the MRI: 1) MRI environment induced interference in the vital sign monitoring equipment; 2) inadequate monitoring of respiration due to long separation between the patient and equipment producing latencies, and blockages in capnograph equipment lines; and 3) use of conventional ferrous-based EKG electrodes and lines cause burns to patients. Therefore the real time control is compromised.

Each of the above problems has been addressed in light of the monitoring equipment. Because the key-monitoring equipment used in detecting the vital signs in the MRI environment is the EKG, a brief interpretation of the EKG waveforms and problems associated with them during the scanning is provided below.

The electrocardiogram (EKG) measures changes in skin electrical voltage/potential caused by electrical currents generated by the myocardium. This electrical activity is typically represented by PQRST waveforms. The P wave reflects atrial depolarisation, while the QRS complex represents ventricular depolarisation, and the T wave ventricular repolarisation. Repolarisation is a process that occurs in many cells where the electrical potential across the cell membrane returns from the value during the action potential to that of the resting state (the resting membrane potential). Although the EKG shows heart rate and rhythm and can indicate myocardial damage, it does not directly give information on the adequacy of contraction. Normal electrical complexes can exist in the absence of cardiac output, a state known as pulseless electrical activity or electromechanical dissociation (EMD). The pulseless behavior is a special case of the myocardium but generally there is a direct correlation between the electrical activity as measured by the EKG with the mechanical activity as measured by phonocardiography. The foregoing is known to those skilled in the art and described in, "Phonocardiography: Measurement of Heart Sounds", www.seas.smu.edu/~cd/EE5340/lect20/tsld011.htm, which is incorporated herein by reference in its entirety.

The EKG is generated using the 3, 5 or 12 lead configuration depending on the circumstances. For example in the MRI, usually 3 or 5 lead EKG is used because the patient is imaged while sedated but does not undergo surgery. At the end of each lead is an electrode that measures the small potential difference produced as a result of heart's electrical activity. By measuring for example the Rate, Rhythm, Impulse Axis, Hypertrophy and Infarction, information about the heart condition can be determined. These characteristic parameters are determined from the data manifested in V1 through V6 leads placed on specific locations on the chest and 1, 2, 3, AVR, AVL and AVF leads placed on the limbs, etc. Normal and abnormal rate and rhythm EKG waveforms that could be used to monitor vital signs as well as to determine other heart conditions are known to those skilled in the art and described in the article "Normal Sinus Rhythm", www.rchc.rush.edu/rmawebfiles/abnl%20rhythm%20for%20parent %20body.htm and www.rchc.rush.edu/rmawebfiles/EKG%20for%20parents%20body.htm, which are incorporated herein by reference in their entireties.

Using the empirically correlated data not only provides clinical information about the five aspects of the heart's electrical activity but also provides variations that reflect other heart conditions associated within each of the five categories. It is well documented in the literature that the P wave signifies the generation of electrical impulses from the SA node, which travels down the AV node into the myocardial cells. The QRS complex represents the electrical impulse when it travels from the AV node into the Purkinje fibers into the myocardial cells and produces ventricular contractions. This signal can therefore provide information about the mechanical contraction of the heart's ventricles, which is followed by its relaxation (process of repolarization). This characteristic signal when used by itself or in conjunction with other waveforms reveals many heart conditions such as arrhythmias, abnormal rates and infarctions; provided the EKG waveforms are not corrupted.

A number of manufacturers such as HP, Colin Medical etc. make vital sign monitoring systems that are frequently used in operating rooms and outpatient surgical environments. These systems provide continuous monitoring capability of the EKG, pulse oximetry, blood pressure, respiration rates via end-tidal $CO_2$, etc. However, it has been observed that these monitors do not work well in the MRI environment. It is found that the EKG waveform is corrupted due to strong static magnetic fields, RF pulses, and the TVMF. For patients oriented in the supine position in the MRI scanner (Anesthesia Equipment in the MRI Suite", Charlotte Bell, MD and Rebecca Dubowy, MD, Department of Anesthesiology, Yale University School of Medicine, New Haven, Conn., USA. www.gasnet.org/mri/about/about-mri3_br.phb), the following effects are observed in the output EKG waveforms and the associated hardware:

1. The static magnetic field induces maximum voltage-charges in the conducting blood column within the transverse aorta since it is 90 degrees to the field (Peden, et.al. 1992 cited in "Anesthesia Equipment in the MRI Suite, Charlotte Bell, MD and Rebecca Dubowy, MD, Department of Anesthesiology, Yale University School of Medicine, New Haven, Conn. USA"). These charges are superimposed on the EKG waveform and are observed to be greatest in the ST segments and T waves in leads I, II, V1, V2 elevating the waveforms. The elevation of the waveforms increases with increasing magnetic field strength and can mimic EKG changes of myocardial injury.

2. Spike artifacts that mimic R waves of the EKG are produced when the magnetic field gradients are applied for imaging the tissue along with the RF pulses. These artifacts can simulate arrhythmias and produce an error in heart rate.

3. The pulsed RF field produces heating of the leads and electrodes (Catheters and Guide wires in interventional MRI: Problems and Solutions, M. K. Konings, et. al, Medica Mundi, 45/1 March 2001).

The first two effects corrupt the true EKG waveform and make it difficult to interpret the patient condition while the third effect causes skin burns. As a result, several MRI compatible EKG monitoring systems have been developed utilizing EKG electrodes and leads made of carbon graphite vs. the typical Ag/AgCl. The carbon graphite material is used to lower resistance at these RF frequencies and eliminate ferromagnetism so that the interference induced heating is minimized. Additionally, filters are used in the signal processing to minimize artifacts. Although using graphite electrodes, special filters, ensuring cable straightness, and placing towels on the patient's chest minimizes the skin burns, the false R spikes, elevated ST segment and T waveforms are still manifested in the EKG when the magnetic field gradients and RF field are applied.

Other techniques such as Pulse Oximetry Plethysmography have been used as a heart tachometer (mechanical motion sensor), but they are not useful for ischemia or arrhythmia detection. They provide delayed response and are unable to discern all four heart sounds. Telemetry units have been used with low magnetic fields (0.6T), but generally interfere with the RF needed for imaging (Barnett, et. al. 1988, McArdle, et. al. 1986 cited in "Anesthesia Equipment in the MRI Suite", Charlotte Bell, MD and Rebecca Dubowy, MD). Therefore, the presence of false R spikes, elevated ST segment and T waves give incorrect rates and rhythms, which leads to misinterpretations and misdiagnosis and makes it impossible to reliably detect ischemia or arrhythmias (ventricular or atrial flutter/fibrillation); the worst two life threatening conditions. Because presently there are no alternatives, for patients that are highly susceptible to ischemia and arrhythmias, a 12-lead EKG pre and post MRI scanning is recommended. If an unstable condition arises, the patient is removed from the magnetic field for proper EKG analysis and treatment, which is the common procedure as suggested by the MRI panel.

For respiration monitoring, the airway adapter based capnograph requires long tubes between the patient and the monitoring equipment. These not only get plugged due to patient mucous but also introduce unacceptable data latency and therefore cannot be used in reliably measuring respiration. To eliminate data latency, long tubes were replaced with fiber optic sensors that were mounted in the airway adapter and could replace the electrical sensors at the end of the tubes to directly measure the airflow. Optovent RR 9700 builds a fiber optic based device, which detects the respiration rate by measuring the flow of air via an airway adapter vs. chest wall movement using inductance plethysmography. Although this technology is immune to the MRI environment, it is insufficient to eliminate the adapter blockage. Additionally, adapter based sensors are invasive and are uncomfortable, producing logistical and control problems during the procedure.

Clearly EKG and airway adapter based technologies that are electrical in nature are insufficient and unreliable for detecting the vital signs (rate, rhythm and respiration) during MRI scans because of the presence of artifact spikes, elevated ST segments that corrupt the interpretation and delayed response with insufficient resolution. This greatly impedes the reliability of monitoring the vital signs especially in patients that are sedated or have heart conditions. Therefore, different technologies are required in the MRI environment that are neither electrical in nature nor are airway adapter based for the measurement of heart rate, rhythm, and respiration. Reliable data must be continuously processed from the uncorrupted R–R' intervals and the QRS characteristics for the myocardial information while a different method to measure respiration is required.

2. Background of Monitoring in Confined Care Facilities

A class of patients (usually but not exclusively elderly) are mostly confined to their beds or rooms for periods of time during their treatment or monitoring such as at elderly care facilities, nursing homes, hospice and convalescent homes, sanatoriums or insane asylums, centers for recovery from drug and alcohol abuse and related facilities (referred to herein as "confined care facilities"). These patients require substantial or constant oversight to monitor their well-being and whereabouts within the facilities usually over the long term. Ideally, a nurse or other caregiver would attend the patient's bedside at all times. However, it is generally impractical and uneconomical to provide this level of care at these facilities. Typically, a few staff personnel serve many patients periodically checking on the status of individual patients. Because the caregivers/staff are not constantly aware of the condition of each patient, serious problems can develop. A patient may leave their bed, either intentionally or accidentally. Even if intentional, the patient may take a fall or become disoriented without being able to timely press the emergency button to seek help. Dementia patients wander off from their rooms or the facility altogether making it difficult for the staff to determine their whereabouts. With only periodic visual checks by the staff and no capability to determine their whereabouts, the patient may be exposed to extended periods of physical and/or mental distress before being located and rendered help to prevent untimely deaths.

3. Background of Vital Sign Monitoring in Hospitals

Continuous and real-time measurement of human physiological parameters, such as respiration, heart rate, blood pressure and oxygenation, can be essential to the preservation of life in numerous clinical settings, including the operating rooms (OR) during procedural sedation, in intensive care units (ICU) and recovery rooms. Indeed, in most industrialized countries, law mandates real time continuous measurements of multiple physiological variables in a variety of clinical situations. Different types of instruments are used to monitor such variables depending on the clinical setting. For example, it is common to monitor heart rate using a 3 or 5 lead electrocardiogram (EKG), respiration rate by end-tidal (end-expiration) volume $CO_2$, blood pressure with an invasive catheter or sphygmomanometer, and oxygenation with a pulse oximeter.

Unfortunately, several continuous monitors of physiological function (e.g., continuous blood pressure using an intra-arterial catheter and a transducer apparatus) are associated with considerable risk and/or extreme costs. For example, continuous measurement of arterial blood pressure requires a skilled physician to introduce a catheter into an artery, while complications include necrosis of the limb, and systemic life-threatening infections. As there is presently no suitable non-invasive alternative, more than one million intra-arterial catheters are placed per year. Another example, pulmonary artery catheters, are introduced directly into the heart and may cause sepsis, ventricular dysrhythmias, and pulmonary artery rupture, all of which are associated with a very high mortality. Indeed, there are an estimated 100,000 cases of catheter-related sepsis and death per year in the U.S. alone. Like intra-arterial catheters, approximately one million pulmonary artery catheters are used annually, at a cost exceeding $1000 per patient, due to lack of a low-risk alternative.

Blood pressure (BP) is a parameter of utmost importance that cannot be measured continuously, non-invasively (NI) and accurately. Because of the potential threat of complications, risk to the patient and extreme costs involved, physicians must compromise on the choice of monitoring selected. They either settle for measuring blood pressure non-invasively on periodic intervals, accepting that the procedure gives discomfort to the patient and is not continuous, or choose the invasive approach if conditions warrant such utilization. If a non-invasive method is chosen, the measurement is generally performed using the "auscultatory/oscillometric inflation technique" which is regarded as the "Gold Standard" worldwide. The instrument used is either the manually operated "cuff and puff" sphygmomanometer or an automatic one. The automatic versions of these instruments provide blood pressure data on a periodic cycle but not continuously. The periodic cycle is programmable by the user from 1 minute to 8 hours or more. These instruments used are considered non-ideal for the following reasons: 1) BP cannot be measured continuously; 2) the patient experiences discomfort due to frequent squeezing of the arm to occlude blood flow and 3) false alarms or erroneous data are produced due to patient motion induced artifacts. These problems greatly interfere with the sleep/rest cycles especially during recovery or after sedation or at nighttime in an intensive care unit.

Other instruments, such as developed by COLIN-Europe for continuous NIBP monitoring, use several point sensors in a cuff configuration that are piezoelectric in nature. The piezoelectric sensors output electrical signals in response to mechanical movements such as that produced by the arterial wall. These devices have the following disadvantages: 1) the sensors are not passive and therefore cannot be used in environments such as the Magnetic Resonance Imaging (MRI) and Computer Tomography (CT) scan because they are affected by Electromagnetic interference (EMI), magnetic fields and Radio Frequencies (RF); 2) they generate erroneous data because the piezoelectric sensors are sensitive to mechanical shocks; and 3) they need to be continually aligned with the arterial wall, and calibrated frequently since they are not distributed area sensors.

SUMMARY OF THE INVENTION

1. Use of Fiber Optic Interferometric Vital Sign Monitor in MRI Environment

The fiber optic sensor of the present invention discussed in detail below, measures the acousto-mechanical activity when the fiber is placed in close proximity with the body, in particular the myocardium sounds (S1, S2, S3 and S4) and the respiration rates simultaneously. Heart and respiration rates of a patient are two vital sign parameters that must be detected reliably during MRI scanning. A single or plurality of the inventive sensors may be used for listening to both the normal and abnormal heart sounds (S1, S2, S3 and S4) in addition to detecting the respiration rate. Because the first heart sound represents the closure of both the mitral and tricuspid valves and also represents the initiation of ventricular contraction or systole, it is generated within tens of milli-seconds after the EKG's QRS complex and can be used to determine the heart rate. In the same way, the S2 sound represents the closure of both the aortic and pulmonary valves and represents also the initiation of the ventricular relaxation or diastole occurring at the same time as the T wave in the EKG. Because the S1 sound is strong, it can be used to measure the heart rate more accurately than with the EKG. Absence of S1 sound or abnormal sound would suggest heart problems. In such a case, the patient may be removed from the MRI, an EKG administered without the magnetic fields along with life saving CPR etc. Therefore, in one embodiment, multiple optical sensors may be affixed to the patient's chest around the apex, atria and ventricles to measure the heart sounds/rate, which is facilitated by a microprocessor based counter and recorder.

The inventive fiber optic sensor may also be used to supplement the EKG information by reprocessing corrupted data. For example, multiple optical sensors and graphite electrodes (optrodes) may be packaged together and simultaneously affixed to the patient's chest at the atria, apex and ventricles similar to when recording an EKG. The output signals from both the optical sensor and EKG electrodes are then correlated and processed to eliminate unwanted spikes and the elevated ST segment and T wave from the EKG waveforms. Different schemes to process these signals may be used such as fast Fourier transforms or time correlation filtering techniques to process the data.

The inventive fiber optic interferometric sensors may also be combined with other sensors used in MRI to monitor sedated patients. These sensors include the following: optical pulse oximetry to measure partial pressure of oxygen or heart beat; non-invasive and invasive blood pressure sensors; capnographs or end-tidal volume $CO_2$ for respiration measurements; and temperature measurements.

The inventive fiber optic sensors may be configured in a jacket or mattress pad to monitor the vital signs non-invasively as described below. These could be combined with the EKG and other monitoring devices for compensating data.

2. Use of Fiber Optic Interfermetric Vital Sign Monitor in Confined Care Facilities In confined care facilities; the inventive fiber optic vital sign monitor described below may be used to provide a means of immediate notification to the staff when a patient has left their bed. Of course, a patient doesn't have to leave bed to experience difficulties that require immediate attention from the staff. Accordingly, the fiber optic monitor can also provide immediate notification to the staff when there is a significant deviation in either their breathing or the heart rate from normal. In situations when a patient may have left the bed, the inventive fiber optic sensor, when supplemented with an RF or IR transmitter device, may provide the whereabouts of the patient within the facility and sound an alarm in certain cases.

These and other objects are achieved by this aspect of the invention, which employs a combination of the passive inventive fiber-optic interferometer sensor system and an RF or IR transmitter that is issued to the patient on checking into the facility. The fiber optic sensor system continuously monitors the patient's vital signs (including heart and breath rate) and provides immediate notification to the staff in case either rate goes outside of prescribed bounds, or in case the patient leaves the bed and the rate signals are lost, whereas the RF or IR transmitter emits a patient Identification (ID) code that is picked up by RF receivers installed in the room, bathroom and hallways to determine their whereabouts.

A sensor pad comprises the optical fiber that responds to acousto-mechanical movements of the patient. No connections (wires, fibers, or tubes) to the patient are necessary. The patient merely lies on the bed and the sensor pad responds to the micro-movements caused by the patient's heartbeat and breathing. Two optical fibers packaged in a single cable emerge from the sensing pad and connect to a Fiber Optic Signal Conditioning Box. The box includes the following: a light source that sends light through the fiber coil in the sensing pad; a detector that converts the light that has traveled through the sensing coil into an electrical signal; a processor that extracts the breath rate and heart rate from the modulation of the detectors signal; an interface communication module located in the signal conditioning box that sends the results to the local and/or central/monitoring station to provide numeric readouts and alarms; the vital sign signals may be transmitted over exiting power lines, wireless radio link or new phone lines, cable lines, local area network lines.

A battery operated short range RF or IR transmitter cuff emits the patients ID periodically at preset intervals. This cuff is placed on the patient's wrist or leg, for example. The code is unique and is emitted in serial time segments in such a way that there are no message collisions between the IDs of various patients within the facility resulting in data washout at the receiver. Short-range RF or IR receivers located within the bedroom, bathroom and hallways pick up these unique signals. Because the range of these receivers is limited, the presence of a signal indicates the proximity of the patient. The receivers perform the following functions: they detect and process each patient's ID code; an interface communication module in the receiver transmits the message consisting of the processed ID codes and location of each patient to the central monitoring station; the messages may be transmitted over exiting power lines, wireless radio link or new phone lines, cable lines, local area network lines.

At the central monitoring station, information about the patient is generated using both the vital sign and the RF or IR signals that have been processed using a signal processor. This information for each patient can be provided as follows: a graphical display of the breath rate; a numeric display of the breath rate; a graphical display of the heart rate; a numeric display of the heart rate; a numeric display of the patient's location within the facility or visual display such as a point representing in real time the location of the patient on a graphical map of the facility.

Different alarms are communicated, in the form of a text message, a flashing light, an audible signal, or any combination. All or any portion of the above information set may be displayed/output at either the local or the remote Readout Interface. The location of the local readout interface may be in the patient's room.

Different communication links are established for each patient within the Confined Care Facility to communicate the heart and breath rate outputs of the Fiber Optic Monitor to the Central Station from the local readout. In addition, the RF or IR Receiver output that detects the location of the patient within the room, bathroom or hallways is provided to the Central Station.

3. Use of Fiber Optic Vital Sign Monitor in Hospitals

Considering the problems described regarding vital sign monitoring in hospitals, there is clearly a need for better instruments that can provide blood pressure (BP) and other physiological functions non-invasively, continuously and accurately. Therefore, one of the primary objectives of this embodiment of the current invention is to provide non-invasive monitoring of BP with continuous readouts using minimal squeeze pressure that ensures comfort to the patient. It is yet another objective of the invention to provide a continuous readout of the patient's heart rate along with BP, and provide alarm notification if the levels deviate from prescribed bounds. A secondary objective of the invention is to provide features such as the following: automatic alarm notification if the BP level exceeds the prescribed bounds; a threshold that releases air pressure in case the system malfunctions; and built in test (BIT) for fault detection, and visual or audio indications for proper operation and any malfunctions.

These and other objects of this aspect of the present invention are achieved using the all-passive fiber-optic sensor based on optical interferometer, which is described below. Because the fiber optic sensor responds to acousto-mechanical signals, it can be used to continuously and non-invasively monitor patient's blood pressure, heart rate and respiratory rate. One aspect of the invention is on the use of a single sensor in measuring two of the three functions;

namely the blood pressure and the heart rate. The system consists of the following: inflatable cuff with integrated fiber optic sensor; controls and signal conditioning unit; central monitoring station, and communication link.

A cuff is used to measure both the blood pressure and heart rate non-invasively and continuously. The cuff may be inflated or deflated using an air pump that is located outside the cuff in the controls unit. The fiber optic sensor is integrated within the cuff in such a way that they can be wrapped lightly around the patient's arm or leg with a preload that is required to detect pulsation of the arterial wall. High sensitivity, distributed area sensing and immunity to EMI, RFI, etc. are some of the key advantages offered by the fiber optic sensor of this aspect of the present invention. Airlines may be employed for inflating or deflating the cuff using a microprocessor driven servo control pump system that is located in the controls unit.

The Controls and Signal-Conditioning unit includes various elements one of which is an LED that sends light through an input fiber optic lead into the sensor located in the sensing cuff. A detector converts the light returned from the sensor into electrical signals via a second fiber optic lead. A servo control pressure system actively monitors and regulates the hold down pressure in the cuff. A microprocessor provides automatic calibration of the system, initiates the step sequence command to determine optimum hold down pressure, applies algorithms for noise minimization and drift control, conducts built in test, and provides safety pressure threshold limits, blood pressure and heart rate data storage, processing, and manipulation. The Controls and Signal-Conditioning unit provides local numeric and graphical displays and alarms. A keypad is used through which a user can interface with the system for set up and calibration. A communication link module sends the data to the local and/or central monitoring station to provide numeric readouts and alarms. The link could be over existing power lines, a wireless radio, existing or new phone lines, cable lines, and local area network lines.

At the central monitoring station, information about each patient is recorded and reported to the staff. The following information as a minimum can be provided for each patient: a graphical display of the blood pressure vs. time; a numeric display of the current blood pressure reading; a graphical display of the heart rate; a numeric display of the heart rate.

Different alarms may be provided, which can be in the form of a text message, a flashing light, an audible signal, or any combination. All or any portion of the above information set can be displayed/output at either the local or the remote Readout Interface.

Multiple patients monitored by a single remote readout station may be located at the staff desk typically within the same room. Results from the individual patients can be communicated to the central station using standard communication protocols such as RS485, and Ethernet that allow a single receiving station to monitor multiple sources. The communication can be over copper wires, optical fibers or wireless or in any other manner discussed herein.

BRIEF DESCRIPTION OF THE DRAWINGS

For a more complete understanding of this invention, reference is now made to the following detailed description of the embodiments as illustrated in the accompanying drawing, wherein:

FIG. 15 is a block diagram showing a general embodiment of the invention for use in confined care facilities;

FIG. 16 is a block diagram of the inventive noninvasive blood pressure monitor and heart rate monitoring system used in applications including post operative recovery.

DETAILED DESCRIPTION OF THE INVENTION

Figure 1:
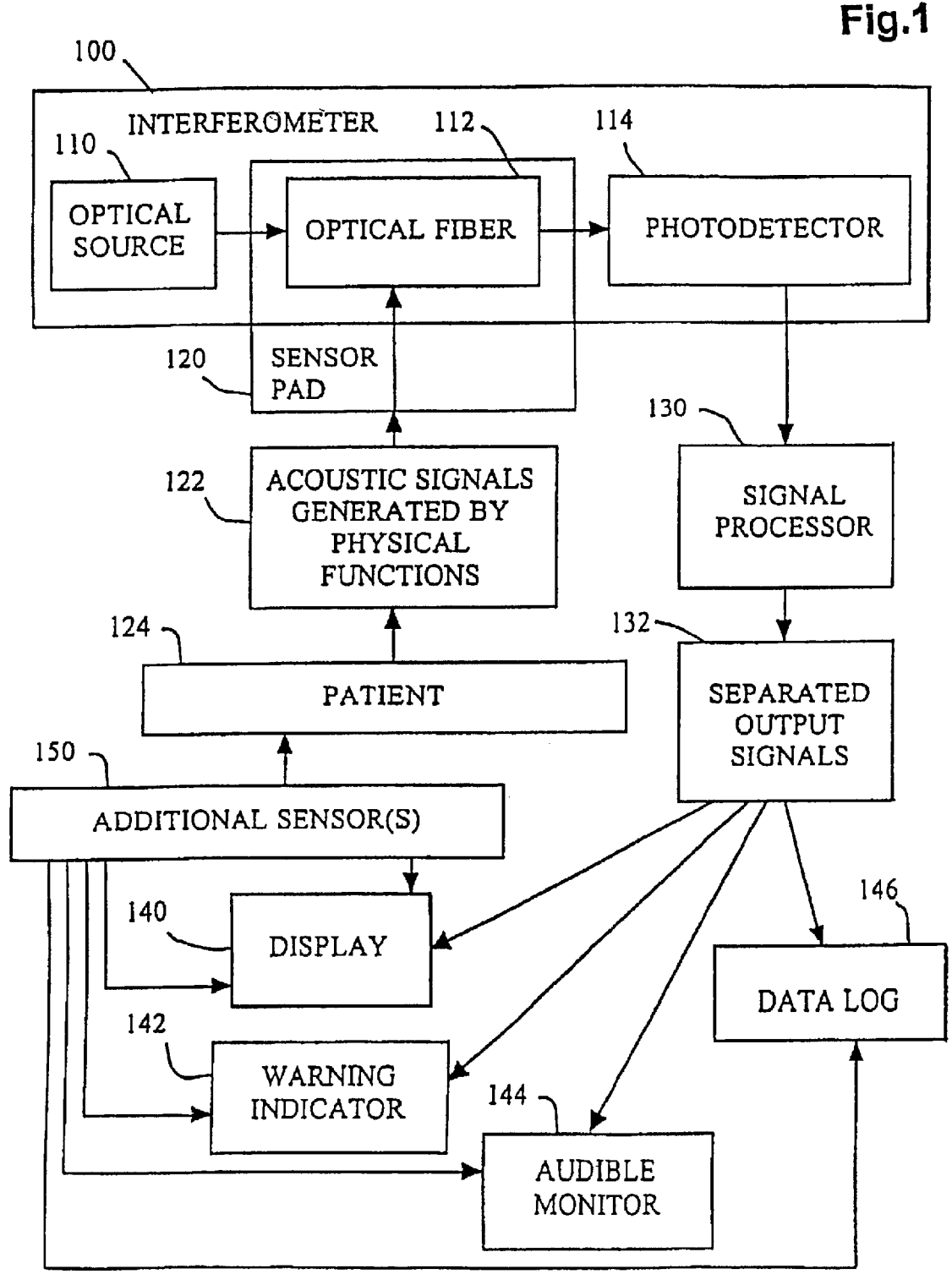
FIG. 1 is a block diagram illustrating an interferometric fiber optic monitor for detecting heartbeat, respiration, and physical movement in a patient.

This invention is described in the following description with reference to the Figures, in which like numbers generally represent the same or similar elements. However, no inference should be drawn in comparing elements, based merely upon the numbering that is used. The sections including A. Overview, B. Description, C. Optical Fiber Sensor Design, D. Fiber Optic Interferometers, are directed to a description of the inventive fiber optic vital sign monitor used in all embodiments of the present invention as described in parent application Ser. No. 09/499,889. After this discussion, the remaining text is directed to discussion of the alternative embodiments of the present invention as found in the following Sections below: 1. MRI Environment Embodiment; 2. Confined Care Facility Use Embodiment; and 3. In Hospital Use Embodiment.

As used herein, the term "patient" is used in its broadest sense to include any living creature that has vital functions or other activities that generate characteristic acousto-mechanical signals. Although the monitor may be described herein in terms of its applicability to humans, it also may be applied to canines or any other type of animal. All discussions of the sensor pad or jacket throughout this disclosure apply equally well to other casings such as a cuff or patch.

A. Overview

A non-invasive, non-intrusive fiber optic-based monitoring system is disclosed that uses optical interferometry to measure acousto-mechanical signals such as heart rate, breathing rate, physical movement and blood pressure without electrical wires, cables, tubes or anything else 'hooked up' to the patient or animal. The patient simply sits, lays down on the sensor pad, or wears it as a garment or a cuff and the acousto-mechanical signals from the heart beating, breathing (expansion or contraction of chest cavity) or physical movement are measured as minute changes in pressure on the fiber optic interferometer sensor pad. The detected acousto-mechanical signals are processed to separate the heartbeat, breathing, and physical movement signals. The separated signals are then communicated by means such as displays that visually present the signal as actual numbers, flashing indicators, audio tones, or alarm functions if vital signs exceed the preset levels or cease entirely.

The system includes an optical fiber-based interferometer sensor situated proximate to a patient. The interferometer senses vital function signals such as the acousto-mechanical signals generated by the patient. Specifically, vital functions such as cardiac activity, respiration, and movement generate characteristic acousto-mechanical waves that are transmitted through the patient's body to the optical fiber proximately situated to the patient. Advantageously, the fiber optic-based vital sign monitoring system non-invasively and non-intrusively measures the "ballisto-mechanical" response of the patient's cardiac system, the pulmonary system and physical movement.

More particularly, the optical fiber-based interferometric monitor utilizes optical phase measurement techniques to sense the acousto-mechanical signature generated by the body's vital functions. The optical fiber is energized using an optical source and the acousto-mechanical signals generated by the body modulate the light signals due to interference. The time varying intensity emitted from the optical fiber is detected and processed using a photo diode, amplifier and electronics. In one embodiment, the optical fiber is incorporated into a sensor pad, and the optical source and the photo-diode along with the processing electronics are packaged in an assembly (an electro-optic unit) placed close to the sensor pad. When acousto-mechanical pulses propagate in the fiber sensor pad, the length of the fiber changes microscopically (on the order of the wavelength of light) corresponding to the amplitude of acousto-mechanical signal and its characteristic frequency spectrum. The change in fiber length changes the optical path length of the light mode propagating in the fiber. This change in the optical path length is directly related to the optical phase change of the unperturbed light mode, which is modulated by the time varying acousto-mechanical signal. When the modulated optical light signal interferes with the unmodulated optical light signal, at the photo-detector or power coupler/splitter, a fringe (time-varying light-dark output) is generated that changes according to the temporal characteristic of the acousto-mechanical signal. By detecting this intensity change of the fringe as a function of time, the applied time varying acousto-mechanical signal is retrieved. When the convoluted optical signal is processed further, the three intrinsic signals are separated using digital signal processing (DSP) or other electronic circuit techniques and displayed on a monitor or recorder depending upon the application.

Fiber optic technology is widely used for many purposes such as communications and remote sensing of physical processes. Fiber optic-based sensors have many advantages. For example, they are lightweight, rugged and corrosion-resistant. Furthermore, optical signals transmitted through optical fibers are immune to electrical or magnetic interference. Also, because optical fibers are corrosion-resistant, the sensors can be easily sterilized, which is important for medical uses and because optical fibers are passive, the threats of patient electrocution and data corruption that exits with other monitors are eliminated. These advantages and others make a fiber optic-based monitor useful in a variety of environments, such as for example monitoring the vital signs of infants and adults in home, confined care facilities, in-hospital and in military situations. When configured properly, a fiber optic-based monitor can also be used to quantitatively predict body's physical parameters such as fat/weight ratio by comparison of the transmitted heart signals with varying body fat content.

Monitoring both the cardiac and pulmonary responses is important in the prediction and diagnosis of cardiac disorders and/or apneic conditions. Monitoring the patient utilizing a conventional EKG, where an electrical instruction is generated at the heart and regulated by signals from the brain, can provide the patient's cardiac rhythm. However, a good EKG signal does not necessarily guarantee that the heart has produced a good mechanical response during that particular EKG signal. Nor does a train of equal shape EKG signals assure that there was a concomitant train of equal mechanical or ballistic responses. Researchers believe that by exploiting heart's ballistic information in addition to pulmonary information (respiration rate and saturation) may be a key to discovering new ways to investigate and understand the pathological/physiological changes apart from the usual cardiac rhythm generated by existing EKG cardiac monitors and pneumographic pulmonary devices. Subsequently, this ballistic information in conjunction with EKG can be used in the diagnosis of cardiac disorders such as atrial/ventricular fibrillation (arrhythmia), which is a leading cause of death in adults. The fiber optic sensor system disclosed herein can provide the ballistic response of heart, and therefore could be a very useful instrument when used with an EKG. If the system is configured to detect abdominal vs. chest movements, it could be useful to diagnose and detect more accurately pulmonary disorders such as obstructive apnea, which is suspected as a leading cause of death in infants. Therefore it is believed that such a system can be used in conjunction with an EKG and other sensors, and may be useful in wide variety of medical applications ranging from simple monitoring of vital signs to more complex detection, diagnosis and prediction of various medical conditions including atrial fibrillation and obstructive apnea.

In one embodiment, a low cost fiber optic-monitor can be used at home, replacing the commonly used sound monitors that are inadequate especially during sleep periods. The low-cost embodiment can be designed to detect three signals (cardiac, pulmonary, and physical movement) and generate an alarm in the absence of an individual signal or any combination thereof. The three signals may be transmitted wirelessly to a remote unit. A microphone sensor may be added to the monitor to detect and transmit the normal sounds of the infant to this remote unit and/or a camera may be added also. The remote unit is carried around in the house by the parent or other caregiver. The three signals as well as the normal sounds and video image may be displayed in different ways on the remote unit, which is described in more detail elsewhere herein.

In another embodiment, the system can be configured to reliably measure and separate the same three signals even during the presence of body's physical movement, which otherwise would dominate and "wash out" the other two signals. Reliable separation and identification of the signals (cardiac, pulmonary, and physical movement) substantially reduces the false alarm rate by combining information from each of the three separated signals. Such a system may be used in applications varying from apnea detection in high-risk infants to atrial/ventricular fibrillation detection in adults under physician's care. Separation of the signals using various signal processing techniques is described elsewhere herein.

B. Description

Reference is now made to FIG. 1, which is a block diagram illustrating an interferometric, fiber optic monitor. An interferometer 100 includes an optical source 110, an optical fiber 112, and a photo-detector 114. A portion of the optical fiber 112 is incorporated into a sensor pad 120 that is situated to receive acousto-mechanical signals 122 generated by a patient 124. In the interferometer, light from an optical source 110 is launched into an optical fiber 112, and the light is modulated within the optical fiber by the acousto-mechanical signals 122. In response, the interferometer generates a time-varying signal which is detected by the photo-detector 114 producing an electrical signal responsive thereto. The electrical signals generated by the photo-detector are supplied to a signal processor 130, such as a digital signal processor (DSP) that separates the signals as indicated at 132. The separated signals are then utilized as desired. For example, the signals may be supplied to a display 140, a warning indicator 142, an audible monitor 144, and/or a data-logging device 146.

The interferometer 100 can be implemented in many different configurations. For example, a Fabry-Perot interferometer, a Mach-Zehnder interferometer, a Sagnac interferometer, or a Michelson interferometer may be used. Many interferometer configurations are known, some of which are described elsewhere herein. Generally, an interferometer requires at least two optical paths that may be established in a single fiber or two separate fibers joined by a coupler. The light from the optical source is divided between the two optical paths, and the photo-detector detects intensity changes resulting from the interference of the two waves with different phases traveling in the two optical paths. The acousto-mechanical signals 122 modulate one of the optical paths but not the other (or not the same amount), thereby creating a time varying (modulated) signal responsive to the applied acousto-mechanical signals. Some interferometers, such as a Mach-Zehnder interferometer, utilize two optical fibers to provide the two different optical paths, while other interferometers such as a Sagnac interferometer utilize, a continuous single optical fiber into which light from the optical source is injected simultaneously into both ends using a fiber splitter/coupler. Accordingly, the interferometer 110 may comprise a single optical fiber or it may comprise two optical fibers to provide the two different optical paths.

Generally, the optical source 110 comprises any suitable source of light, such as an edge emitting diode (ELED), a light emitting diode (LED), a semiconductor laser diode (LD) similar to those used to read conventional CDs, or a gas laser tube. The optical source is chosen to be suitable for the implemented type of fiber interferometer. For example, a Sagnac interferometer can utilize a low cost ELED while a Mach Zehnder interferometer requires a laser diode of suitable coherence length. Likewise, a Fabry-Perot interferometer may require more highly coherent light sources such as a He—Ne or a DFB semiconductor narrow line-width laser, which is compact in size but expensive compared to a He—Ne laser.

Light is coupled from the optical source 110 into the optical fiber 112 using any suitable means such as direct coupling or an imaging lens. Beam shaping devices may be utilized to shape the beam for more efficient coupling. Utilizing the imaging lens allows about a 10 dB improvement in the signal that is launched into the fiber. In order to further reduce losses, a optical matching index gel may be inserted between all glass-air-glass interfaces. Use of index-matching gel makes the glass fiber interface nearly transparent, which substantially reduces unwanted reflections and optical noise generated from these interfaces.

The optical fiber 112 comprises any suitable fiber, for example it may be a single-mode, multi-mode step index fiber, or a graded index fiber. Generally, the type of fiber is determined by the type of interferometer and other design considerations. The choice of optical fiber is described in detail elsewhere herein.

The photo-detector 114 detects the optical signal at the far end of the optical paths in a conventional manner and converts them into equivalent electrical signal. In one embodiment, the optical fiber is butted against the glass window of a single photo-detector that has an active area large enough to accept the cone of light emanating from the fiber or directly to the chip with the glass window removed. The detector may be mounted using a SMA, FC, ST connector or other connector configurations or in a non-connectorized housing.

The sensor pad 120 (or other casing such as a patch or cuff as described below) positions at least part of the length of the optical fiber 112 proximate to the patient 124, where it can receive the acousto-mechanical signals 122. Several embodiments of the sensor pad will be discussed, and many others are possible.

The signal processor 130 comprises a circuit that receives the raw electrical signal from the photo-detector and processes it into separated signals 132, which are suitable for the particular embodiment. As previously discussed, the photo-detector detects the periodic intensity changes of the optical signal over time, and generates a raw electrical signal responsive thereto. The amplitude of the raw electrical signal varies in time in accordance with the frequency response of the acousto-mechanical modulation. The raw electrical signal is further processed by the signal processor 130 to provide one or more output signals. The design of the signal processor 130 and its separated signals 132 are dependent upon a number of factors such as the information desired (e.g., heartbeat, respiration, movement, and/or blood pressure), the desired accuracy of the data, and the type of interferometer chosen for the embodiment. For example, a simple analog circuit design for a signal processor may include a low-pass filter and a high-pass filter to separate the heart and breathing signals from movement-related signals. In one such embodiment, such as described with reference to FIGS. 9A and 9B, the low-pass filter outputs a breathing signal (shown in FIG. 11 whereas a high pass filter outputs a heartbeat signal such as shown in FIG. 12.

Another example of a signal processor 130 is a digital signal processor that converts the raw electrical signal into a digital signal and then processes it using digital signal processing techniques to separate the signals into three or more components such as heartbeat, respiration, and physical movement. Such signal processors can be highly sensitive, and can be implemented in a number of ways, such as a programmed microprocessor, a dedicated ASIC (Application-Specific Integrated Circuit) and/or a computer. Digital signal processing techniques such as autocorrelation, fast Fourier transforms, and/or pattern recognition coding may be used. Furthermore, sophisticated processing techniques may be used, such as artificial intelligence-based programs may be trained to recognize the pattern of particular events of interest, such as an impending apneic event, or an impending heart attack, and provide a warning signal responsive thereto. Such a signal can be particularly useful to quickly trigger an alarm if the recognized event is life-threatening, such as an impending heart attack in an adult, or an impending SIDS event in an infant. If the recognized event is less important, it may simply be recorded.

The separated signals 132 are then transmitted via a suitable interface to an appropriate output device, such as the display 140, warning indicator 142, audible monitor 144, and/or data logger 146. In some embodiments the separated signals 132 may be communicated by a wire connection. Alternatively or in addition thereto, a suitable wireless communication system may be used to transmit the separated signals 132 from the signal processor to any of the output devices.

Figure 2:
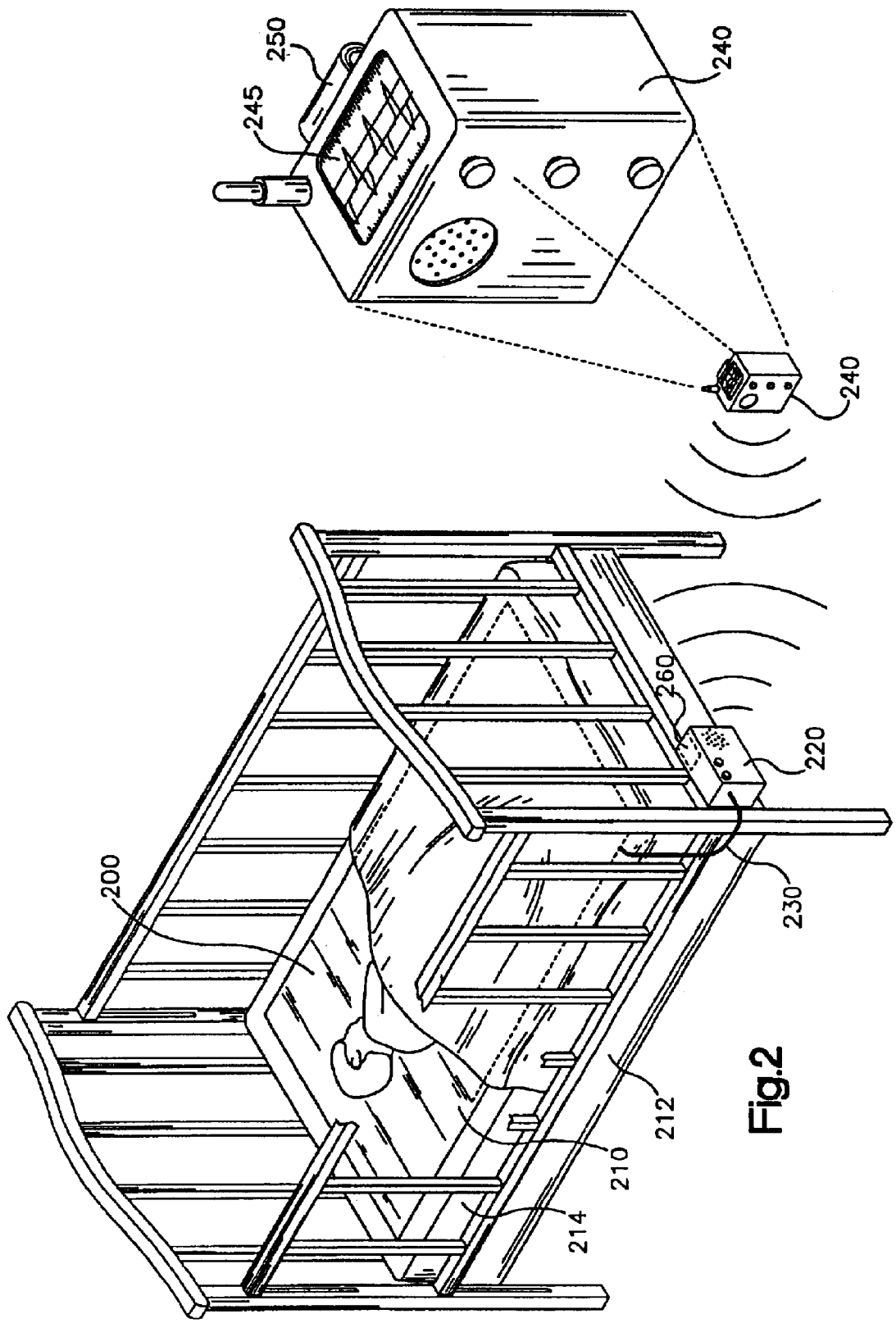
FIG. 2 is perspective view of an embodiment of a fiber optic sensor for detecting the heartbeat, respiration, and physical movement of an infant in a crib, including a portable device for remotely monitoring the infant.

In some embodiments, additional sensors 150 may be utilized to monitor physical parameters of the patient in conjunction with the fiber optic interferometer. Examples of these additional sensors include a microphone, a camera, an oxygen sensor, a carbon dioxide sensor, an EKG system, and a second (or plurality of) fiber optic interferometer(s). Reference is now made to FIG. 2, which is a perspective view of an embodiment of a fiber optic sensor for detecting the heartbeat, respiration, and movement of an infant 200. In this embodiment, the sensor pad has a rectangular configuration 210 designed to fit into a crib 212, and the optical fiber situated within the sensor pad is generally configured in a pattern from side to side along the entire length of the pad. The sensor pad is placed on top of a mattress 214 and optionally under the bed sheets. The infant lies on the sensor pad, which effectively couples the acousto-mechanical signals generated by the infant's vital signs into the optical fiber within the sensor pad. Advantageously, the sensor pad is not hooked up to the infant directly, which allows the infant to shift his/her position within the crib while still being monitored. An electro-optic unit 220 affixed to the crib houses the optical source, photo-detector, signal processor, and other circuitry. The sensor pad is coupled by an optical fiber interconnect 230 to the electro-optic unit. The separated signals are transmitted via a transmitter such as a RF transmitter in the electro-optic unit to a remote receiver such as the portable unit 240 that displays heartbeat and/or respiration on an LCD display 245. The battery-operated receiver can be carried by a parent, doctor, nurse, or other individual, and in some embodiments includes a system for generating audible or visual warning signals responsive to predefined conditions, such as reduced heartbeat or cessation of breathing for more than a preset time. The embodiment illustrated in FIG. 2 includes a belt clip 250 for easy portability. The portable unit can be used in conjunction with a desktop unit (not shown in FIG. 2) that could be placed on a nightstand or in the vicinity of the guardian, parent, or caregiver.

In order to ensure the integrity of the communication link between the electro-optic unit and the remote unit, a fail-safe communication may be used, such as a handshaking routine implemented in the two units by using a two-way RF link and also provide an input for an alarm condition. The electro-optic unit and/or the remote receiver can also provide a blinking LED, an LED array or an LCD responsive to the heart rate and breathing for the monitored infant. In the case of an alarm condition, such as the absence of heart rate, or breathing, or movement, the alarm will be activated. Many different alarm types are possible, for example, a beeper, a voice response unit, or a vibrator may be actuated to alert the guardian, parent or caregiver that a serious condition exists.

In addition to the fiber-optic based sensor, some embodiments may utilize an additional audio system, such as a microphone sensor 260 connected along with an RF transmitter, both of which are located in the electro-optic (e-o) unit in the embodiment shown in FIG. 2. The microphone may be integral to the e-o unit, as shown, or may have another form, such as integrated within the pad itself. The microphone 260 detects the normal sounds of the infant and transmits them wirelessly to a remote unit 240. Such a configuration, in which the microphone sensor simultaneously monitors the infant's sounds described herein, can be useful to provide higher confidence to the parent or other caregiver especially during periods when the infant is awake and moving around in the crib.

Figure 3:
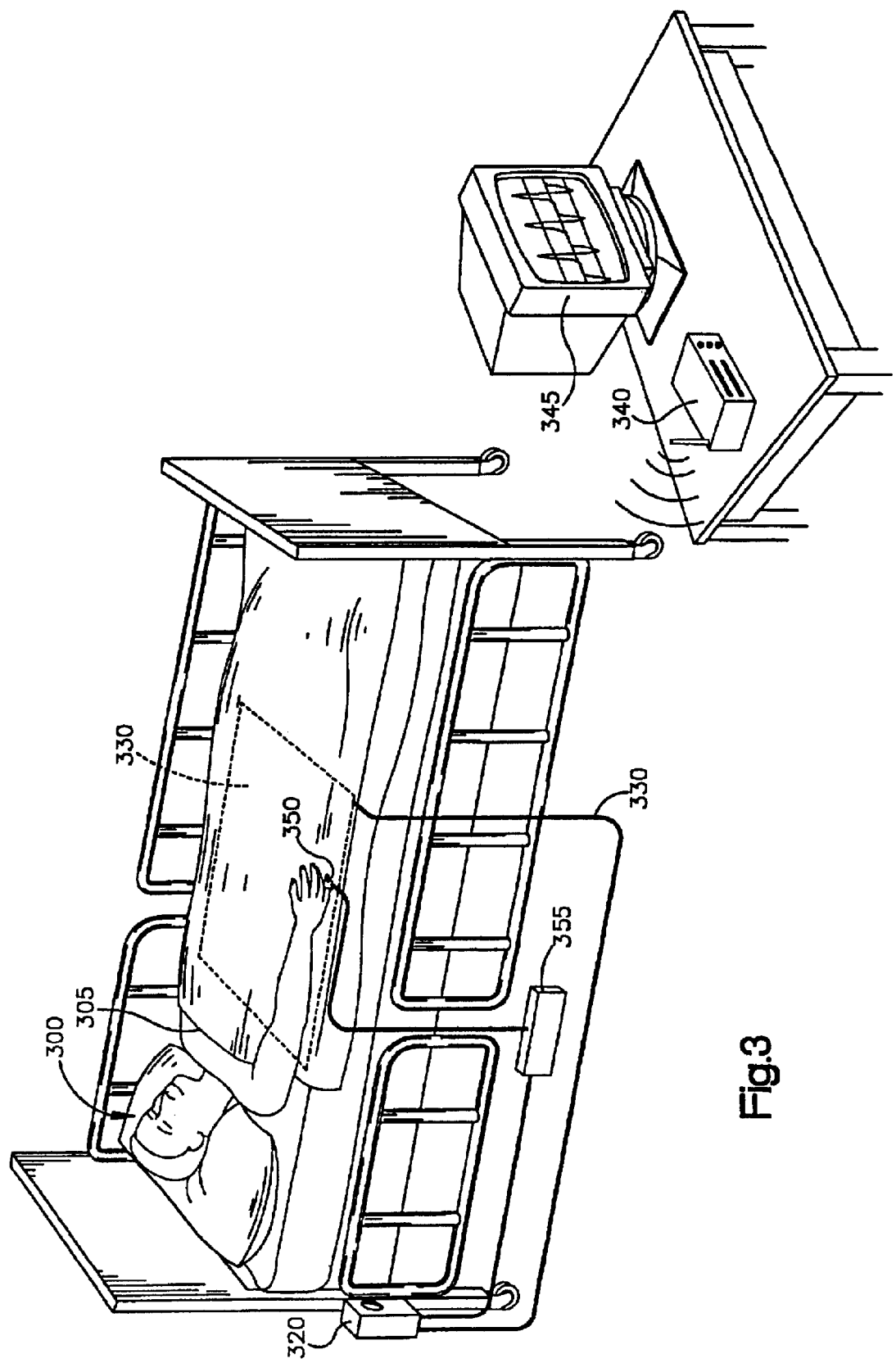
FIG. 3 is a perspective view of an embodiment of a fiber optic monitor for detecting the heartbeat, respiration, and physical movement of a patient confined to a hospital bed.

Reference is now made to FIG. 3, which is a perspective view of an embodiment of a fiber optic sensor for detecting the heartbeat, respiration, and movement of a patient 300 confined to a hospital bed 305. In this embodiment, the sensor pad has a rectangular configuration 310 shown by dotted lines designed to fit under the section of the patient's body near to the heart and lungs. The sensor pad is placed on top of a mattress 312 and optionally under the bed sheets and the optical fiber situated within the sensor pad is configured generally in a zigzag pattern from side to side along the entire length of the pad. The patient lies on the sensor pad, which effectively couples the acousto-mechanical signals generated by the patient's vital signs into the optical fiber within the sensor pad. Unlike other monitors, the sensor pad is not hooked up to the patient directly, which allows the patient to shift his/her position within the bed while still being monitored. An electro-optic unit 320 affixed to the bed houses the optical source, photo-detector, signal processor, and other circuitry. The sensor pad is coupled by an optical fiber interconnect 330 to the electro-optic unit. The separated signals are transmitted by any suitable means, such as a radio signal or a cable, to a remote receiver 340 that displays heartbeat and/or respiration on a CRT monitor 345. The receiver can be situated in a nurse's station, for example. The receiver may also include a system for generating audible or visual warning signals responsive to predefined conditions, such as reduced heartbeat or cessation of breathing for more than a preset of time.

In addition to the fiber-optic sensor, some embodiments may utilize an additional sensor, such as an oxygen sensor 350 that is affixed to the patient's finger to detect the levels of saturated oxygen or carbon dioxide in the patient. The oxygen sensor 350 is connected to a suitable monitoring unit 355, which may in turn be connected to the electro-optic unit 320. Such a configuration, in which the finger-situated sensor simultaneously monitors the patient with the fiber optic monitor described herein, can be useful to more accurately detect apneic events. Additional sensors can be utilized in other embodiments to include an EKG, either alone or in combination with the oxygen sensor.

In some embodiments, the sensor pad 310 and the electro-optic unit 320 include two or more fiber optic interferometers so that two or more separate optical fibers are situated to receive acousto-mechanical information from the patient. The multiple fiber optic interferometers can be utilized for a variety of reasons, such as to provide greater accuracy and sensitivity and in some cases to detect obstructive apnea.

Figure 4:
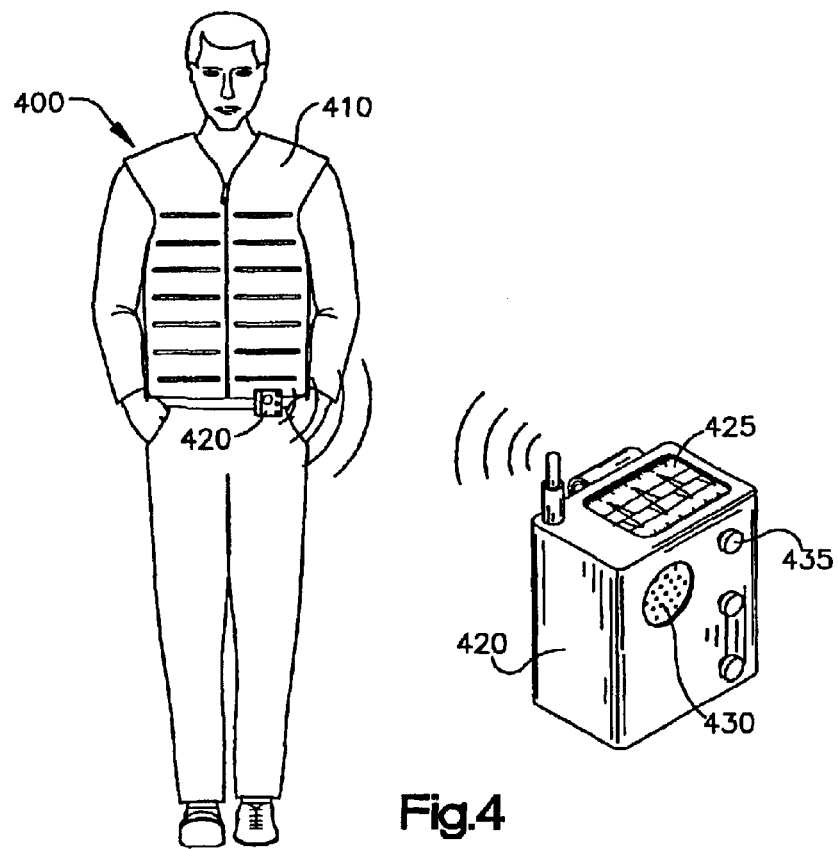
FIG. 4 is a perspective view of an embodiment of a fiber optic monitor for detecting the heartbeat, respiration, and physical movement of an ambulatory patient.

Reference is now made to FIG. 4, which is a perspective view of an embodiment of a fiber-based sensor for detecting the heartbeat, respiration, and movement of an ambulatory patient 400. In this embodiment, the sensor pad is configured or stitched into a garment 410 that is designed to be worn like a vest, which advantageously allows the person to be mobile and not constrained to bed. The garment has a configuration that situates the embedded optical fiber in close enough proximity to the patient's body to couple acousto-mechanical waves into the optical fiber. The sensor pad in the garment is coupled by an optical fiber interconnect to an electro-optic unit 420. The electro-optic unit 420 is carried by the patient, and houses an optical source, a photo-detector, a signal processor, and other circuitry. The electro-optic unit may comprise a visible display such as an LCD monitor viewable by the patient, and may also include a system for generating audible or visual warning signals responsive to predefined conditions such as speaker 430 and an LED or LED array 435. In alternative embodiments, the signals from the electro-optic unit may be transmitted by any suitable means, such as a radio signal or a cable; to a remote receiver such as in a nurse's station or other centralized location.

Advantageously, the sensor pad can be made of materials that are relatively soft, water proof/resistant and comfortable, which is particularly useful in the garment configuration shown in FIG. 4 as well as in the mattress configurations of FIGS. 2 and 3. Another advantage is that the optical fiber and sensor pad can be rolled and stored without damaging the embedded optical fiber. The size of pad can be made to fit a crib, or a full size bed. In operation, the pad can be either placed on a mattress (infant/adult), under the bed sheet and secured using elastic bands and/or Velcro at each corner, or stitched into a patient's garments. Thus, the sensor pad remains substantially invisible to the patient, reducing physical damage and avoiding negative psychological effects.

C. Optical Fiber Sensor Design

To design a sensor pad as described herein that uses optical phase interferometer for detecting the vital signs of the human body or canines, it is useful to determine the optical fiber sensor length required to adequately detect the acousto-mechanical pressure generated by the heart beat or respiration.

In Sagnac sensor configuration, maximum sensitivity can be achieved by making the sensor length approximately half the delay coil length. However, by limiting the phase change, it is empirically found that a fiber sensor length of about 10 to 20 meters is adequate to detect heart and respiration signals of both infants and adults. Longer fiber lengths can provide higher detection sensitivity because the sensing area under the patient is increased for the same acousto-mechanical signal. But by trading off the phase change against the fiber length and the pad area for a given acousto-mechanical pressure, the sensor designed may be optimized for a specific application.

Optical Fiber Embodiments

In designing a sensor pad using an optical fiber, several factors must be considered, such as minimizing optical attenuation in bends (macroscopic as well as microscopic), ensuring the fiber is mechanically rugged so that it does not fail when bent, and efficiently coupling of the fiber to the optical source.

Although many types of optical fibers can be used, two different embodiments of optical fibers are of particular interest: a single mode step index fiber and multi-mode graded index fiber. Both optical fibers are made from fused silica glass, have excellent optical and mechanical properties, and produce minimum optical attenuation in tight bends. In one embodiment the single mode fiber is 7/125/250/900, for example. In another embodiment the multi-mode graded index fiber is 62.5/125/250/900, for example. The 250 micron diameter buffer is a UV acrylate and 900 micron is made from an elastomeric polyester. Suitable optical fibers are manufactured by Corning Glass of Corning, N.Y. Both fibers have excellent mechanical properties when subjected to bends. Mechanically, the fiber should not fail when subjected to bends in the pad. Because the minimum bend radius of this particular fiber is approximately 0.25 inch, it is adequate for use in a pad configuration, which has bends much greater than 0.25 inch. If the bend radius used in the pad is 0.825 inches, the bend stress can be calculated as 31.5 kpsi based on the relationship that $S=Er/R$. This bend stress is three times less than the proof strength, which warrants a fiber life greater than 30 years and approaching 40 years using the fatigue resistance parameter of about 20. This is in agreement with the measurements provided by a leading manufacturer, Spectra-Corning, Avon, Conn., where the stress level required for a forty year life is about 34.5 kpsi using $n=20$. However, for fibers with $n=30$, such as Corning's Titan (titanium doped) single mode fiber, the bend radius can be small as 0.52 inch for a 40 year lifetime. Fibers with 80 microns OD compared to 125 can have even smaller bend radii and still maintain a 40 year life expectancy.

In one embodiment, the sensor pad fiber life expectancy at bend radius of 0.825 inch is better than 30 years. Additionally, since this fiber is proof tested to 100 kpsi at the factory, freak fiber failures are screened. The fiber life and strength can be improved further by utilizing surface clad coatings such as titanium-doped silica, hermetic diamond-like coatings and/or hard polymeric coatings.

The sensor fiber required must exhibit low optical losses due to bending. The excess loss in the fiber is less than 1 dB from the first five 0.5 inch diameter bends and almost no loss beyond that. As is known to those skilled in the art, to minimize optical bend losses it is desirable to use a large numerical aperture (NA) fiber. Large NA fibers are less susceptible to macro bending/micro bending losses as they can contain the light even at large bend angles minimizing the leakage of light from the core to clad and into the buffer. In this case, the graded index fiber had an $NA=0.27$, whereas for the single mode has the NA of about 0.1. It was observed that when a patient rested on the pad, no significant loss could be measured. However, the system is designed to operate with optical losses of approximately 20 dB, of which 2–3 dB could be due to body weight.

The single mode fiber was evaluated to further investigate the possibility of enhancing the fringe visibility while reducing signal fading. The single mode fiber can provide improved interferometric sensor performance over a multimode design because of the absence of signal mixing and/or coherent superposition summing between adjacent spatially transverse wave-guide modes. Therefore the signal mixing and subsequent signal fading is substantially reduced although not completely eliminated. It is believed that if a polarization preserving single mode fiber wave-guide is used, the signal fading can be essentially eliminated. However, because of the high cost of the polarization preserving fiber, one compromise is to use a short section of the polarization preserving fiber along with the single mode fiber.

Either single mode fiber or multimode fiber can be used depending on tradeoffs associated with the interferometer type chosen, the sensitivity desired and the design cost goals. For example, multi-mode fibers can be easily coupled to a diode source requiring less touch labor compared to coupling single mode fibers that require careful design considerations to optimize the optical throughput. However, when trading off performance, the single mode fibers provide much better fringe visibility (sensitivity) compared to that achieved using multi-mode fibers.

Sensor Pad Embodiments

Although for the reliable detection of both heart and respiration signals in infants and adults, many configurations of the sensor pad are possible, only two are discussed below. There are four basic design principles implemented in the design of the fiber optic pads. First, it should be mechanically rugged so the optical fiber embedded in it does not break when folded, flexed, cleaned or due to body weight/movements. Second, it should not produce safety hazards. Third, the fiber should stay in place and cover the entire area of the pad so that the patient may move around freely without any restrictions. Fourth, the manufacturing design of both the optical fiber sensor pad and the interconnect lead should be cost effective.

In a first sensor pad embodiment, the optical fiber is stitched on a fabric substrate and encapsulated in a soft but durable plastic casing/shell for protection. The casing resembles a pillow cover-like configuration, with three sides closed and the fourth side open. To allow the fiber-sensor pad to conform to the contour of the human body, optimize mechanical displacement for respiration detection and achieve good coupling to detect heart signals, an appropriate size foam rubber sheet was added on the underside of the substrate before encapsulation. After encapsulating the fiber stitched substrate and the foam sheet into the casing, the fourth side of the casing is closed using conventional stitching. Alternatively, this step may be done using heat-sealing at the edges. The fiber is allowed to exit on one corner of the substrate after it is strain relieved into the substrate along with the interconnect tubing.

A typical heavyweight fabric can be chosen as the substrate on which the fiber is integrated. The fabric is cut to size for a typical rectangular crib and the edges of the fabric are stitched together. Following this procedure, a number of piping channels (0.5 inch wide by 18 inch length) are made from the same material, then cut to size and stitched into the substrate separated from each other by 1.75 inches. These channels were sewn normal to the length of the fabric. In this configuration, seventeen optical fiber channels were created to allow the fiber to zigzag through the channels for the entire length of the substrate. The channels in this sample are stitched to the substrate such that they will provide sensor coverage for the full length of the patient's body. The piping channels are left open at the ends for threading the optical fiber from one channel into the next. The optical fiber was then threaded through these channels and the exposed U-shaped configuration of the fibers each end are subsequently covered and stitched into place. The fiber sewn fabric substrate is then slipped into the pre-fabricated casing. The fourth side of the casing is temporarily closed and the ingress and egress of the fiber to the casing is confined to one corner of the casing where it is strain relieved. Accidental bending and flexing of the optical in a radius less than 0.25" is restricted by the use of foam placed under the substrate.

The casing is made from a quilted plastic material that is designed to be area larger than the substrate to allow easy insertion into the substrate. This material is quite rugged, water-resistant and fire retardant. After cutting two sheets of material to size, the sheets are conventionally stitched together at three sides and the fourth side is left open for sensor substrate insertion. Such a pad configuration may be further enhanced for improved signal coupling from young infants with body weights so low that the pad does not flex enough to get good signal coupling. Enhancement may be achieved by affixing the fiber sensor pad across a frame of appropriate thickness and size suspending the pad above the surface, leaving an air gap between the pad and the surface. This configuration allows the infant to flex the pad in the air gap, thereby providing better signal coupling.

In a second sensor pad embodiment, the same heavy weight fabric for integrating the optical fiber is used as in the first embodiment. However, the difference in the second design is that the pad size is made much smaller and two straps are added on the sides of the pad. One purpose of the straps is for better detecting the chest and abdomen breathing of the patient and for better securing the pad to the patient. In addition, the material used to cover the sensor substrate is different, because the pad is worn as a garment where factors such as comfort, feel and fit are given more importance. The under side material of the straps is carefully selected also to ensure that the straps do not slip when locked in place on the body. This material is silicone based and is stitched in to the straps. The width of the straps is about one inch while the length is adjustable.

The optical fiber is stitched into the pre-cut substrate using the previously described piping channel approach. The piping channels are stitched into the substrate in such a way that the fiber enters the substrate in the middle, makes a 120 degree turn and then goes down the length of the strap. At the end of the strap, the fiber makes a U-turn and then goes into the other strap of the same set. After making a turn in this strap, the fiber is routed into the pad area where it is serpentine and then routed through the next set of straps similar to the first one. It is important that the fiber routing between a set of straps is continuous to ensure that the breathing induced strain is directly coupled into the fiber and while the heart pressure pulses are coupled in it.

Sensor Pad Manufacturing Design Embodiments

The fiber sensor pad or the integrated garment may be manufactured using the conventional molding and sealing approaches. In a mold having fingers spaced appropriately, a material of right compliance and compressibility such as high-density foam is positioned. Optical fiber is then strung in a zigzag fashion (manually or with a robotic arm) into the mold around the fingers. After stringing the fiber, a second sheet of the same material is placed over the fiber such that the strung fiber is sandwiched between the two sheets. Heat is then applied to seal the two sheets to form the composite fiber sensor pad.

In one embodiment, it is envisioned that the production design includes a continuous zigzag pre-grooved rubber/foam substrate, which is encapsulated in a plastic casing after the installation of the fiber. The fiber is installed in the groove using UV-curable soft RTV or other equivalent adhesive. Selecting the right adhesive is useful to reduce microbending stresses in the fiber due to temperature variations that would otherwise contribute to excess optical signal attenuation. The groove depth in the foam substrate is approximately half the size of the overall diameter of the fiber (1 mm). In such a configuration, approximately half the fiber in the groove would appear above the substrate and the rest would become part of the substrate after installation. The rubber substrate, therefore, has two different sides. One side of the substrate has the fiber secured in the grooves (the sensing side), while the other side is flat without containing the fiber. In this fashion, the pad does not have raised rib-like structure but is relatively smooth providing further protection from damage. The sensor substrate is then encased in an outer protective plastic sheet. The two outer sheets are heat sealed by conventional plastic welding technology, which advantageously prevents entry of liquids or moisture into the optical fiber sensor substrate while also achieving high strength. In operation, the fiber-exposed side of the substrate is placed directly under the patient to achieve good acousto-mechanical coupling.

In one embodiment of the pad, the optical fiber is used in a double-jacketed configuration, in which an extra protective coating is applied over the first jacket. This second jacket can provide additional mechanical strength to the fiber and prevents breakage since it limits fiber bending. The extra protective coating over the 900 micron polyester jacket increases the diameter of the fiber to about 1.8 mm. The increase in diameter of the fiber does not pose any problems in manufacturing. In fact, it is desirable to use larger diameter fiber because of the ease in handling the fiber during manufacturing process. Presently, the fiber is used without a second jacket and as a result requires custom repackaging and strain relief to protect the inter-connection between the pad and the electro-optic unit.

If the second jacket is applied on the fiber using pressure-extruded technology developed by Optical Cable Corporation, the acoustic energy can still be efficiently coupled to the glass fiber with minimum coupling losses. This is achieved because the glass fiber is tightly coupled to all strengthening members (the buffer, first jacket and the second jacket), allowing efficient coupling of acoustic signals between any gaps or voids between the jackets and the buffer. Nevertheless, depending on the absorption coefficient of the jacketed material, one might expect some signal attenuation at these low acoustic frequencies, which could be optimized by proper choice of material combinations.

Using a double jacket fiber configuration in the pad has two advantages. First, the process of custom interconnection between the pad and the electro-optic unit is eliminated. Secondly, the mechanical strength of the fiber is improved. Furthermore, in such an embodiment it may not be necessary to use a three-hole polyvinyl tubing to strengthen and protect the fibers at the transition interfaces and prevent breakage. This translates into cost savings because it reduces both the number of parts and the manufacturing steps, while increasing the reliability and quality of the sensor pad.

D. Fiber Optic Interferometers:

The invention is designed to employ fiber optic interferometer, which can take many forms. More specifically, the Fabry-Perot, Mach Zehnder, Sagnac, or Michelson interferometers discussed below, can be configured in the invention to detect the aforementioned acoustical signals. Optically, the fiber optic interferometer determines the optical wave phase shift with respect to a reference optical wave phase. Optical phase shift(s) are generated via strain or pressure-induced length change and/or refractive index change in the fiber optic sensor arm, leg, or optical fiber path of the particular interferometer configuration. Herein, fiber optic interferometry can be described by the principle of two-beam interferometry, which allows the measurement of ultra-small differential phase shifts in the optical fibers as generated by the applied acoustic signals. The total phase delay ($\phi$) of light propagating through a fiber is given by:

$$\phi = nkL \tag{1}$$

where n is the effective group refractive index of the fiber core, k is the vacuum optical wavenumber ($2\pi/\lambda$) with $\lambda$ being the optical source wavelength, and L is the physical length of the fiber. The optical path length ($L_{OP}$) is given by:

$$L_{OP} = nL \tag{2}$$

As with all single mode fibers above their natural cut-off wavelength, there are actually two orthogonal polarization modes that exist within the fiber mode field diameter, the space in and around the core where the electromagnetic wave fields are confined. Generally, due to birefringence effects that take place within bent or otherwise non-ideal deformed fibers, the polarization state is elliptical. Because of the high clad-to-core diameter ratio in single mode fibers, much of the orthogonal polarization mode power exists within the clad region of the fiber and, as such, can be easily tapped via evanescent field coupling devices, for example power splitters and combiners that are disclosed herein. However, in order for fringes to occur at maximum efficiency (visibility) all polarization states must be substantially identical at the point where the two beams are combined.

Ultra-small variations in the phase delay $\phi$ are found by the differentiation of equation # 1 such that $$d\phi/\phi = dL/L + dn/n + dk/k \tag{3}$$

of which the first two terms are related to physical changes in optical fiber caused by acousto-mechanical perturbations (heart, respiration, and/or physical movement) that are to be measured. Accordingly, the first two terms describe the transduction mechanism by which fibers act as sensors. Generally, changes in pressure, position (displacement), or temperature, for example, may result in different contributions to $\phi$ via the dL/L and dn/n terms.

Because the fringe is at maximum efficiency (visibility) only when the polarizations of the interfering beams are substantially identical, any polarization shift in one of the interfering beams with respect to the other will reduce efficiency. Such reduced efficiency, occurring over a period of time, leads to fading of the fringe; a problem that is addressed in detail elsewhere herein.

Fabry-Perot Interferometer:

A common form of interferometer is the Fabry-Perot (FP) interferometer, which was first constructed in the late 1800s by Charles Fabry and Alfred Perot. It is a very useful device because it provides an extremely high-resolution capability to measure displacements, and it can also be used as a spectroscopic device.

For purposes of illustrating the operating principles of a Fabry-Perot interferometer, a large-optic free-space Fabry- Perot multibeam interferometer will be discussed first. The large optic device comprises two parallel plane semi-reflecting mirrors which are separated by some distance, d. When a single coherent ray of light is launched from one side of the partially reflecting mirrored surface, it is reflected multiple times in the gap. For each reflection of the ray from the two interfaces, there is a transmitted ray produced. These transmitted rays combine to form a single fringe on the screen or the detector opposite to the launch side. The intensity of this fringe varies from bright to dark when the gap is varied, mechanically or the medium is altered, because the coherent light beam interferes either constructively or destructively as the separation of the gap (for example) is minutely (on the order of a fraction of light wavelength) varied, producing high or low optical intensity. All monochromatic coherent rays launched at one angle combine to form a single fringe. If an optical detector is placed at this end, it will measure the variation of this single fringe intensity as a function varying gap separation.

For a Fabry-Perot interferometer to be implemented in an optical fiber form, the coherence length of the optical source must be much greater than the length of the sensing fiber. The reason is that light interference will occur at the receiving detector between the optical signals reflected from the first facet of the fiber and those transmitted through the second facet without reflection. Because of the round trip travel distance, the phase difference ($\phi$) between two successively transmitted waves at normal incidence is given by $$\phi = 4\pi n_\phi L / \lambda_0 \tag{4}$$

where L is the length of the sensing cavity (fiber), $\lambda_0$ is the operating wavelength and $n_f$ is the refractive index of the fiber. When the phase difference between two adjacent transmitted waves satisfies the interference condition 2L sin $\theta = n_\phi \lambda$; a standing mode is produced at the detector which is either dark or bright depending on the induced phase shift with respect to the reference phase shift (½ or an integer) with respect to the reference phase. The standing mode does not change when there are no external forces present. However, when an external force is applied and/or the cavity length is altered, the standing mode changes because the transmitted waves experience an additional phase shift. Thus, when L is varied, the above equation is written as:

$$\Delta\phi = 4\pi n_{100} \Delta L / \lambda_0 \tag{5}$$

The time variation in the phase difference produces an interference signal at the detector. Thus the photo-detector measures displacement-velocity-acceleration signals generated by the time varying interference signal, which contains information about the applied acousto-mechanical signal and its repetition rate.

Figure 5:
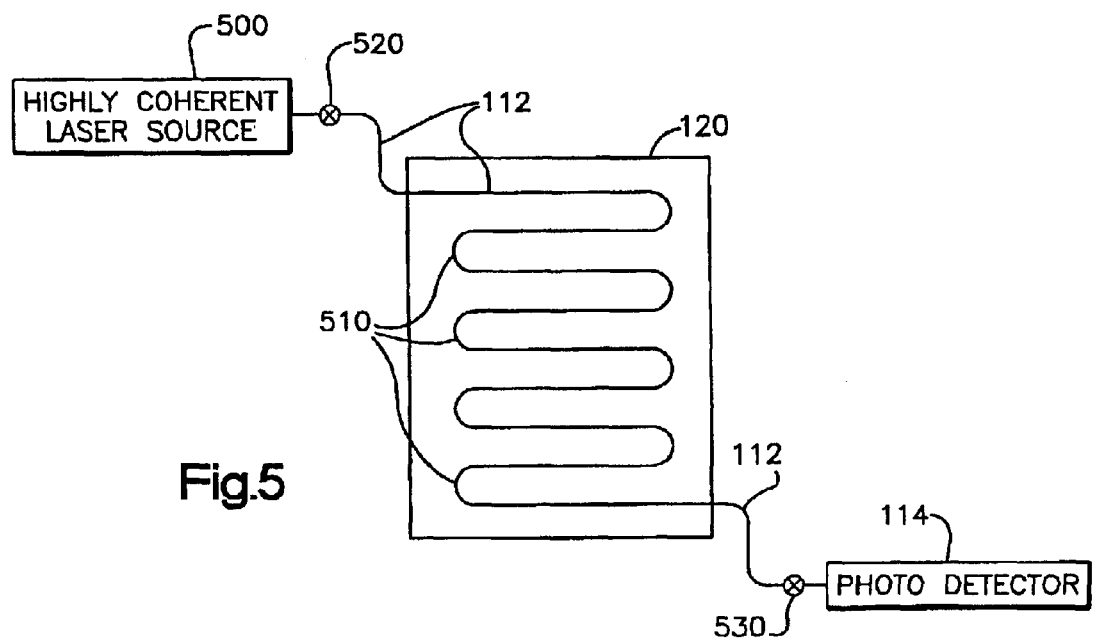
FIG. 5 is a diagram of the interferometer section of a fiber optic monitor implemented with a Fabry-Perot interferometer.

Reference is now made to FIG. 5, which is a diagram of a fiber-based monitor implemented with a transmissive Fabry-Perot fiber interferometer. A reflective Fabry-Perot can also be implemented via a fiber coupler. A coherent laser source 500, such as a He—Ne laser or a DFB laser, supplies a laser beam that is coupled into the optical fiber 112. The optical fiber may be a single mode fiber or a multimode optical fiber made from fused silica, and for example, in one embodiment has a length of about 17 meters. An intermediate length 510 of the optical fiber (10 meters) is embedded into the sensor pad 120. The optical fiber has a first cleaved end 520 into which the laser beam from the laser is coupled, and a second cleaved end 530 is coupled to the photo-detector 114, which defines the cavity for the interferometer. In other words, the two cleaved ends of the optical fiber, which have a reflectivity of about 4%, serve as the two partially reflecting mirrors of the interferometer. Accordingly, the cavity medium is the amorphous glass of the optical fiber, which in one embodiment has a refractive index of about 1.457, and the physical length of the optical cavity is approximately 17 meters since the length of the fiber in this embodiment is about 17 meters. In operation, the incident light from the laser source coupled into the optical source propagates into the core and is partially reflected from the far distal end (the second cleaved end) of the fiber. However, a part of this beam is also transmitted through the second cleaved end and out of the fiber. The reflected light returns to the first cleaved end and then is reflected again. In this fashion, the transmitted light comprises two or more propagating longitudinal cavity modes, which mix and interfere at the photo-detector. The transmitted modes interfere constructively and destructively over time as the length of the fiber is minutely changed by cyclic acousto-mechanical pressure impulses, for example, generated by the heart, respiration or physical movement and applied to the fiber in the transverse direction.

Figure 5A:
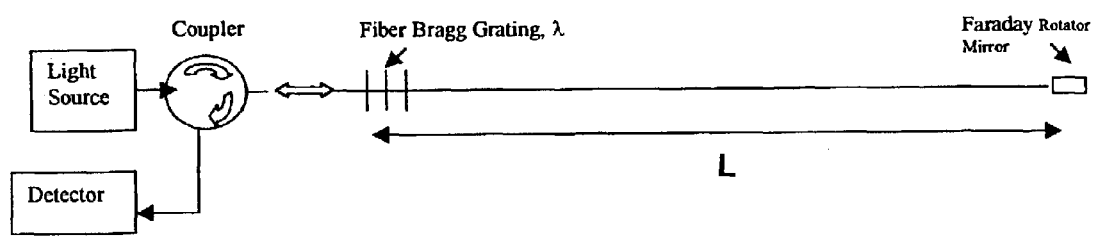
FIG. 5A shows a single wavelength CW single sensor channel Fabry Perot Reflective Architecture using Fiber Bragg Grating and Faraday Rotator.

As shown in FIG. 5a, a FP interferometer may also be constructed using a Fiber Bragg Grating (FBG) or other "partial" reflector, as the "first reflector" and a Faraday Rotation Mirror (FRM), FBG, or other partially or fully reflecting "second mirror." The transmitter and receiver may be configured to operate in continuous wave (CW) operation at one optical carrier wavelength. In this configuration, the reflected light signals from the FBG and FRM interfere to produce a fringe similar to the conventional FP interferometer. By restricting the sensor cavity between 2 FBGs, it is possible to eliminate fiber optic lead noise. Using the FRM as the "second mirror" or two pieces of crossed polarization maintaining fibers allows in the elimination of polarization induced fading effects. The phase front of the reverse (reflected) optical beam will be the "phase conjugate" of the forward incident beam, upon reflection from the FRM. The reflected phase conjugate beam travels the same path, but in the reverse direction, as the incident beam, thus eliminating changes in birefringence along the fiber waveguide from independent environmental effects.

The intermediate part between the two reflectors of the fiber is configured in a zigzag fashion extending from the top of the sensor to the bottom within the sensor pad. The pad is placed under the patient (FIGS. 3 and 4) in order to detect the acousto-mechanical signals generated from heart, respiration and any physical movement. In any particular embodiment, the configuration of the optical fiber within the sensor pad is designed to provide effective coupling of the acousto-mechanical signals into the optical fiber. The detection and isolation of these three signals and post-analysis provides the means to sense apneic events or other abnormalities in patients.

Figure 6:
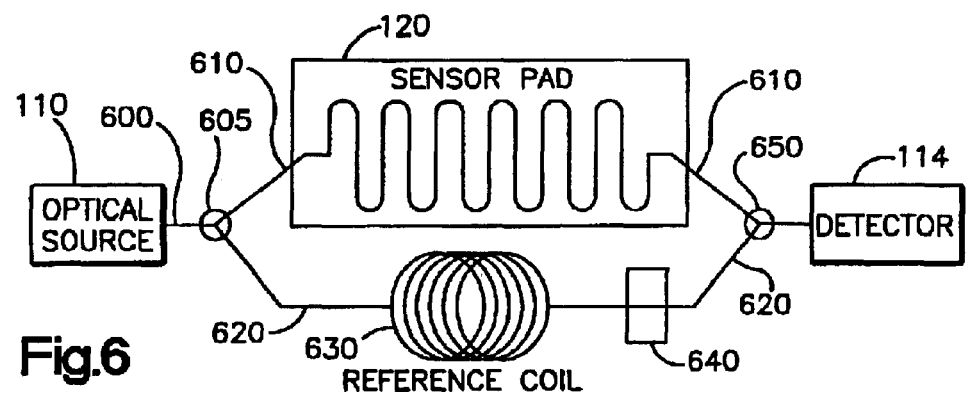
FIG. 6 is a diagram of the interferometer section of a fiber optic monitor implemented with a Mach-Zehnder interferometer.

Mach Zehnder Interferometer:

Reference is now made to FIG. 6, which is a diagram of a Mach-Zehnder interferometer. The optical source 110 supplies coherent or incoherent light 600 which is divided at a first fiber coupler 605 between a first fiber arm 610 and a second fiber arm 620. The first fiber arm 610 extends through the sensor pad 120 and second fiber arm includes a reference coil 630 and a polarization controller 640. The polarization controller can be placed in the sensor arm as well. The purpose of the polarization controller is to maximize signals through all possibilities of polarization in order to prevent polarization induced signal fade. The first and second fiber arms are combined at a second optical coupler 650, and the combined output is then supplied to the detector 114. For the Mach-Zehnder interferometer to operate efficiently, the first and second fiber arms must have nearly the same length, and the coherence length of the optical source must be approximately equal to the actual length difference between the two fiber arms. If the coherence length is too short the fringe pattern will be weak or non-existent, and if the coherence length is too long, phase noise will dominate the intensity variations.

The acousto-mechanically-enhanced pressure variations on the sensor pad 120 create corresponding minute changes in the intermediate length of the fiber in the sensor pad, compared with the reference fiber. When this difference is compared to the optical wavelength of the optical source, tens, hundreds or even thousands of wavelengths may be affected by the pressure changes. By combining the two optical signals at the second coupler and counting the fringe patterns, a conversion from pressure to fringe counts can occur. These fringe patterns may start as very slow changes as is the case with breathing, a little faster for heart rate and very fast for physical movement.

The output intensity of the interferometer incident of the photo-detector may be expressed as:

$$I = \langle E_r^2 \rangle + \langle E_s^2 \rangle + 2 \langle E_r E_s \rangle \quad (6)$$

where $\langle \, \rangle$ denotes the time average over a period much longer than $2\pi/\omega_o$ and $E_r$ and $E_s$ are the optical fields at the photo-detector(s). The intensity varies as the phase of the two signal varies. The efficiency or fringe visibility of the interferometer (assuming identical polarization states exist at the output coupler) is given as:

$$V = (I_{max} - I_{min})/(I_{max} + I_{min}) \quad (7)$$

The actual value of V depends ultimately on the self-coherence function g(t), which is given by $g(t) = \exp[-|t|/t_c]$, where t is the differential optical propagation time delay between the reference and signal paths and $t_c$ is the source coherence time. Therefore, V is always reduced by the factor g(t). For this reason, the differential propagation time delay between the fiber paths is adjusted to be much less than the coherence time ($t < t_c$). Therefore the factor g(t) approaches unity and V is maximum, as determined by the polarization states of the two beams at the combining power coupler.

For fiber-based ASE (Amplified Stimulated Emission) sources, semi-conductor laser diodes without Bragg diffraction gratings, ELEDs or LEDs, the coherence length is fairly small, on the order of hundreds of microns to a few millimeters, and therefore the length difference between the two fibers that provide the two optical paths of the Mach Zehnder Interferometer must be on this order. For some light source choices, the fiber length differences must be measured extremely accurately in order to provide a highly sensitive monitor. One way of accurately measuring this length is to utilize high-resolution optical time domain reflectometers that can provide sub millimeter resolution. Another way of measuring the length, is to use conventional measuring rulers or gauges, which are not as accurate, and would limit the use to a laser diode having longer coherence length than an ELED or LED.

Figure 7:
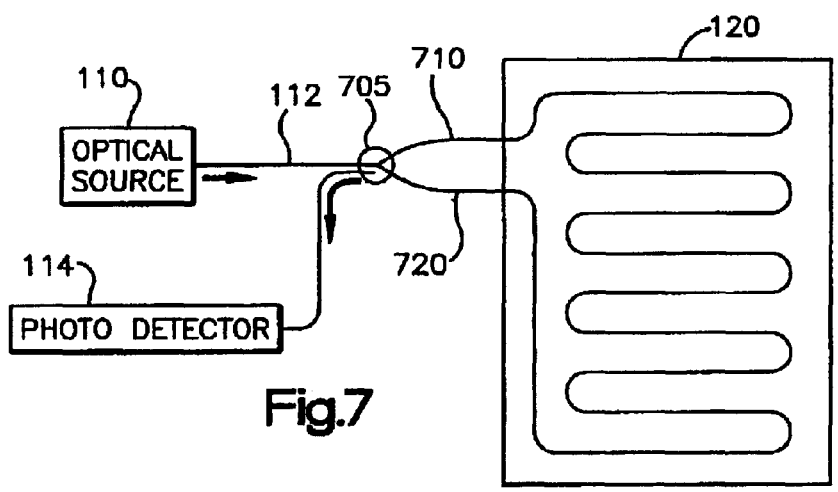
FIG. 7 is a diagram of the interferometer section of a fiber optic monitor implemented with a Sagnac interferometer.

Sagnac Loop Interferometer:

Reference is now made to FIG. 7, which is a conceptual diagram of a fiber optic monitor implemented with a Sagnac interferometer. Because of its common path architecture, a Sagnac interferometer does not convert source phase noise into intensity noise, thereby eliminating a major source of the low frequency noise present in Mach-Zehnder sensors. Also, because of the common-path, and to further reduce noise, Sagnac interferometers can use inexpensive, broadband high-power sources, such as ELEDs, LEDs, ASEs, fiber superfluorescent, and superluminescent diodes, in place of generally more expensive narrow line width lasers. In the Sagnac interferometer, light from the optical source 110 is coupled into both ends of the optical fiber at a coupler 705. Particularly, the light is coupled from the coupler 705 in phase into a first end 710 and a second end 720. Light signals coupled into the first end propagate through the optical fiber to the second end, and light signals coupled into the second end propagate in the opposite direction through the optical fiber to the first end. Both of the light signals then exit at the coupler 705 and propagate together through a fiber section 730 to the photo-detector 114, where the time-varying fringes are produced and measured. In the Sagnac interferometer, the phase shift is measured between the light going clockwise (CW) to the light going counterclockwise (CCW) in a loop of fiber where optical signals are launched in opposite directions in phase.

Figure 8:
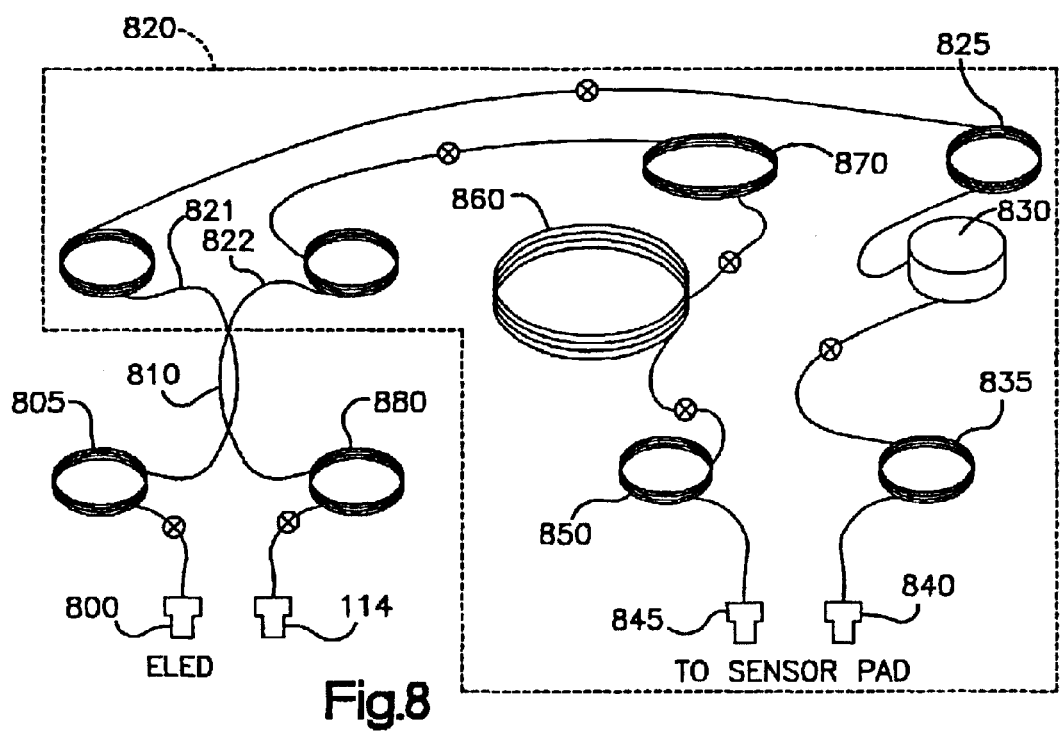
FIG. 8 is a diagram of an alternative embodiment of the interferometer section of a fiber optic monitor implemented with a Sagnac interferometer.

Reference is now made to FIG. 8, which is a diagram of one embodiment of a Sagnac interferometer. The light source comprises an ELED 800 that is coupled to inject light into a first length 805 of optical fiber. A 50/50 coupler 810 is connected to the first length 805, and divides the light so that it is injected approximately equally between a first end 821 and a second end 822 of a fiber optic loop defined within the box 820. Beginning at the first end 821, the loop includes an optical fiber length 825 that has a suitable phase modulator 830 attached thereto. After the phase modulator 830, another length 835 of optical fiber is connected at a first pad interconnect 840 to one end of the optical fiber in the sensor pad 120 (see FIGS. 5, 6 for example). The other end of the optical fiber in the sensor pad is connected to a second pad interconnect 845, which is coupled to another length 850 of optical fiber. This optical fiber 850 is connected to a delay coil 860 that has a length that defines a large percentage of the overall length of the entire loop length inside box 820. The delay coil 860 is coupled to a depolarizer 870, which in turn is connected to the second end 822 of coupler 810.

The counter-clockwise (CCW) propagating beam, after traveling through the delay loop 820, is combined at the 50/50 coupler 810, and then propagates along a final length 880 of optical fiber to the photo-detector 114. The clockwise (CW) propagating beam travels first through the delay loop, fiber, and then through the, sensor fiber, whereas the CCW beam travels through the sensor fiber first and then through the delay loop fiber. During the time delay period between the arrival of the CW and CCW beams at the detector, the perturbation induced phase modulation in the sensor fiber changes. This change in phase modulation is directly proportional to the phase difference between the counter-propagating beams, which generates an optical fringe when the beams combine and interfere at the power coupler.

In an alternative embodiment, the Sagnac interferometer can be implemented to operate in a reflective mode where the transmissive loop is replaced by a single fiber with a mirror at the distal end. Similarly, a single coupler/splitter approach may also be employed to operate in a transmissive mode. Many other configurations are known, some of which are described herein.

Theoretically, if a physical perturbatory signal of angular frequency ω induces a phase modulation $\phi_s \cos(\omega t)$ in the sensor fiber loop, the resulting phase modulation between the interfering beams at the sensor $\phi_{in}(t)$ is then given by:

$$\phi_{in}(t) = \phi_S \cos(\omega t) - \phi_S \cos[\omega(t + T_{delay})] \quad (8)$$

$$= 2\phi_S \sin[\omega T_{delay}/2] \sin[\omega t + \omega T_{delay}/2] \quad (9)$$

where $T_{delay}$ is the time delay between the arrival of the CW and CCW beams at the sensor itself. Thus, the amplitude of $\phi_{in}(t)$ is a function of the sensor phase modulation $\phi_s$ and the product of the perturbatory angular modulation frequency with the loop time delay. This differs from the Mach-Zehnder sensor in which the amplitude of $\phi_{in}(t)$ is a function of only the sensor phase modulation $\phi_s$.

Maximum sensitivity can be achieved in the Sagnac interferometer sensor when the product $\omega T_{delay}$ is an odd multiple of $\pi$. The perturbation frequency that makes this product exactly $\pi$, which is the lowest frequency at which maximum sensitivity is achieved, may be called the "ideal" frequency of the loop. For the ideal loop frequency to be below about 7 kHz, which is the frequency regime of interest for most human and animal body motion sensing applications, a time delay of at least 50 microseconds, and therefore a delay loop length of about 7 km is required. In one embodiment, by trading off the sensitivity and delay loop length, the Sagnac sensor was designed with approximately a 500-meter delay loop and about 20-meter sensor loop.

The phase modulator 830 is utilized to translate the acousto-mechanically-modulated light signal out of the DC region into an AC signal. The phase modulator may be employed in one or both arms of the interferometer. Such phase modulators are commonly used for low frequency audio signal systems. Phase modulators can have many forms, such as a fiber stretcher, which is typically constructed by winding an optical fiber around a cylindrical piezoelectric transducer. The piezoelectric material utilized is typically of the lead-zirconate-titanate (PZT) family of piezoelectric crystals. Other forms of such bulk crystal modulators may be employed, such as PZT disk stacks and bars, which allow for non-coiled fiber stretching. In these PZT embodiments, the fiber to be stretched is linearly attached to the surface of the crystal along the primary polling orientation of the crystal for maximum mechanical force as a function of applied voltage across the crystal electrodes. The PZT cylinders, however, act on the helical turns of fiber via hoop or radial modes of crystal polling. Such phase modulator/shifters serve the function of a voltage-controllable-phase shifter. It is also possible to configure the Sagnac interferometer without a PZT modulator such as using a 3×3 coupler configuration to achieve similar performance characteristics.

The type of optical source plays a role in achieving the ultimate noise performance of any fiber interferometer. As mentioned earlier, the coherence length of the source must be much longer than the length mismatch between the two optical paths of the interferometer. In fact, any mismatch in length between the sensing and reference paths, whether delayed or not, leads to increased intensity noise through a coherent interference process where the phase noise is converted to intensity noise. The phase noise of the source is ultimately the limiting noise factor if any path mismatch is present in the interferometer.

For these reasons relatively broadband sources (tens of nanometer FWHM), such as LEDs, ELEDs, superluminescent diodes (SLD), and amplified spontaneous emission (ASE) superfluorescent, are typically employed in perfectly matched path interferometer circuits, such as the Sagnac loop. Contrarily, narrower band sources (~0.1–5 nm), such as Fabry-Perot lasers, DFB and fiber lasers, are typically employed in slightly mismatched circuits, as are realized in Michelson and Mach-Zehnder configurations.

Signal Fading

There are at least two ways in which signal loss can occur in optical fiber interferometers, not including insertion losses from various fiber components in the optical interferometer circuits. These are: 1) slowly time varying differential phase shifts due to, for example, ambient temperature and pressure fluctuations; and 2) differential variations in the polarization state within the fiber paths, which also can be due to ambient changes in temperature and pressure, but are largely due to uncontrolled rotation/twisting and bending in the fiber.

Twisting and bending in an ordinary single mode, non-polarization maintaining fiber, can lead to birefringence effects in the fiber between the two degenerate orthogonal polarization modes. The resulting differential phase velocities of these two modes produce polarization rotation in one path with respect to the other path, which leads to an effective dot product of near zero between the two interfering optical fields within the output coupler or at the detector, thus producing little or no detectable interference fringes, from an otherwise state of good interference. This reduction in detectable interference fringe signals, due to polarization effects, is generally called "polarization fading or signal fading".

In fiber optic interferometers, the signal fading can be minimized in many different ways. For example, replacing the entire length of the single mode fiber with a polarization-maintaining (PM) fiber can eliminate this problem. However, the cost of using the PM fiber throughout an interferometer is prohibitive for most low cost embodiments. Alternatively, either passive depolarizers or actively controlled polarization controllers may provide a more cost effective solution to adjust the polarization states of the signal and reference paths to minimize signal fading.

The depolarizers or polarization controllers can take a variety of forms, some of which are discussed elsewhere herein. For example, the passive depolarizer may consist of two sections of polarization maintaining (PM) fibers crossed at 45 degrees; whereas controllers may include devices such as 1) multi-axis fiber squeezers to produce controlled birefringence; 2) resistive heater using bimetallic elements to produce controlled birefringence; or 3) high speed polarization mixers or scramblers. These controllers or depolarizers when used in fiber interferometers can provide compensation to cover the complete Poincare Polarization Sphere of the numerous polarization state possibilities.

In operation, the optical fiber in the sensor pad 120 may be subjected to phenomena such as temperature changes and pressure differentials that tend to shift the polarization of the optical signal propagating throughout. As discussed briefly above, any polarization shift in one of the interfering beams with respect to the other will reduce interference efficiency and cause fading of fringes over time because the interference is at maximum efficiency (visibility) only when the polarizations of the interfering beams are substantially identical. Such polarization-induced fading problems can substantially degrade the signal-to-noise ratio and thereby degrade the effectiveness of the monitor. Accordingly, many embodiments of the fiber optic monitor include features to reduce fading, such as the depolarizer 870 shown in FIG. 8. This depolarizer 870 is generally passive or if a polarization controller is used, it may be dynamically driven at frequencies at least twice of any present in the sensor or phase modulation circuits.

In the Mach-Zehnder interferometer embodiment shown in FIG. 6, it is known that the two optical path lengths in an interferometer must be very closely matched. Even if lengths are matched at room temperature during the manufacturing process, temperature gradients between the sensor pad and the reference coil along and/or changes in pressure on the sensor pad independently can shift the polarization of the light beam in one of the fibers with respect to the other. This can be enough to cause the light intensity to fade as a result of the polarization state vector of one arm moving from a parallel orientation to a perpendicular orientation of respective vertical and horizontal components, resulting in cancellation of the desired signal. To minimize this fading, it is necessary to adjust the polarization state of the two arms of the interferometers such that the dot product of the interfering beams in the output coupler is as close to unity as possible. Again, this may be accomplished by employing the polarization controller 640 (FIG. 6), which is generally placed in one arm of the interferometer. To maximize the signal, the polarization controller 640 is adjusted and set once if no further changes are required in fiber circuit physical geometry. However, if the physical layout of one or both paths of the interferometer must change, for example due to deployment logistics or external perturbations, then the polarization controller set point must change accordingly. For this reason in this embodiment, an active slow speed servo-loop feedback circuit is implemented along with the polarization controller in order to maintain maximum fringe visibility.

In the Sagnac interferometer embodiment, which generally utilizes a broadband source, two short sections (less than a couple of meters) of crossed polarization maintaining fibers provide a passive (without quasi-static servo), low cost solution suitable for maintaining the polarization states. On the other hand to achieve equivalent performance in interferometers using narrow band sources, the length of each section of the PM fiber must be substantially increased. For these interferometers, the fiber squeezer type polarization controllers with active control may be more effective in maintaining the proper polarization states and reduce signal fading.

Electro-optic Unit Embodiment

Figure 9A:
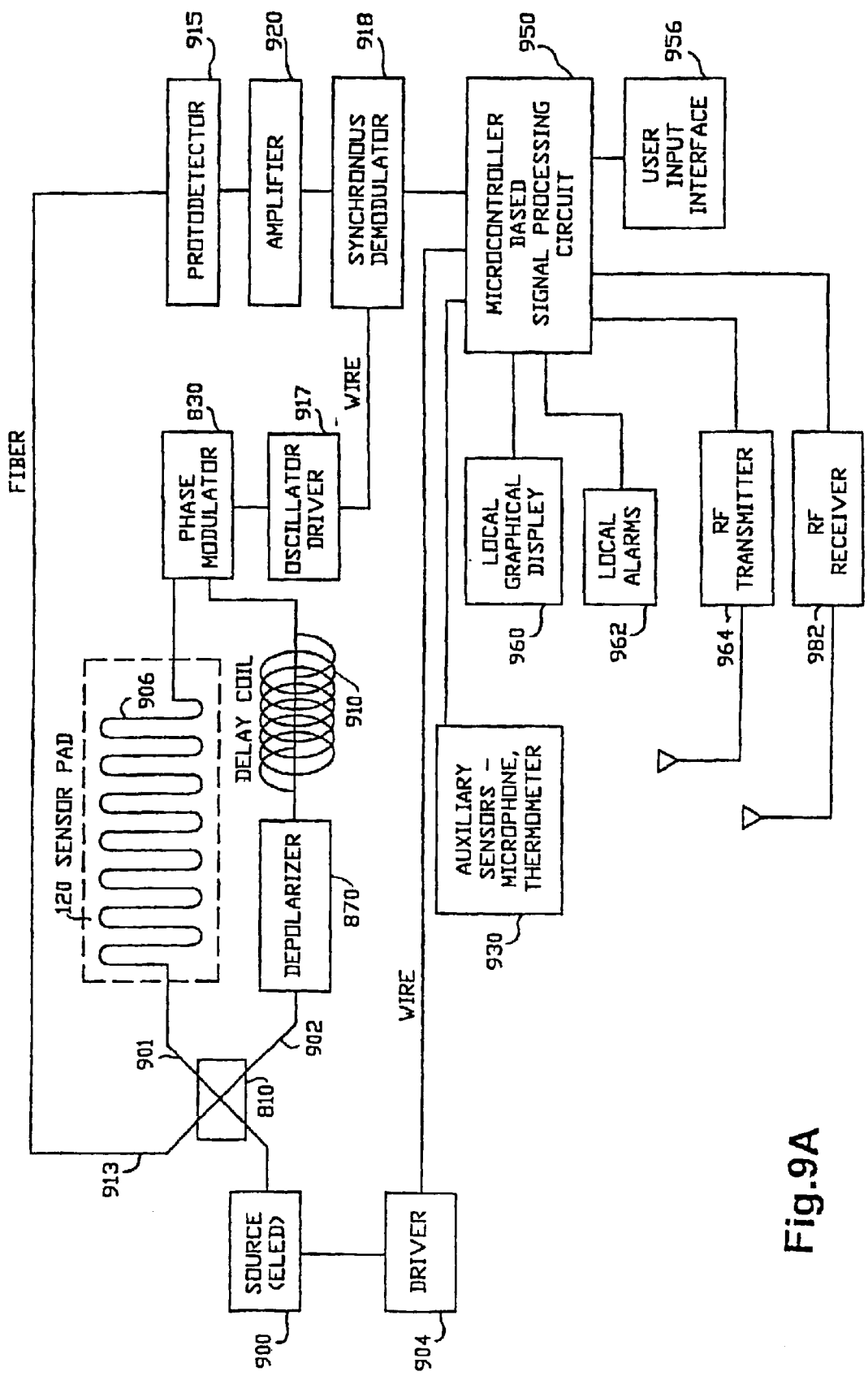
FIG. 9A is a block diagram of the interferometer and associated processing circuitry for one embodiment of a fiber optic interferometer-based sensor in a Sagnac Loop configuration suitable for detecting heartbeat, respiration, and physical movement.
Figure 9B:
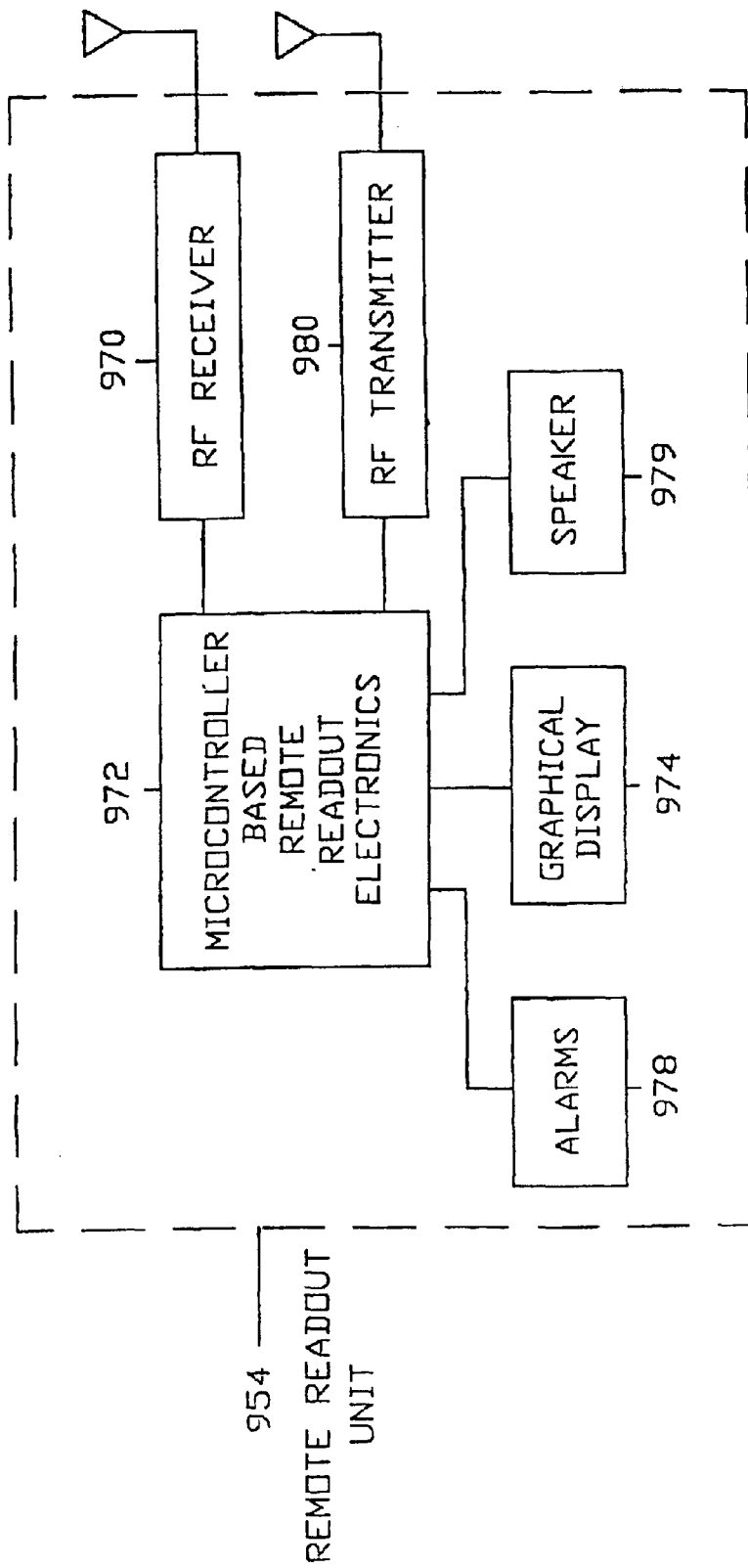
FIG. 9B is a block diagram of a remote receiver unit for receiving separated signals from the processing circuitry of FIG. 9A.

Reference is now made to FIGS. 9A and 9B, which form a block diagram of one example of a fiber optic interferometer-based monitor in a Sagnac Loop configuration suitable for detecting and displaying heart, respiration, and physical movement signals locally at the sensor via the electro-optic unit and remotely via a remote readout unit.

A broadband optical source 900 such as an ELED supplies optical radiation to a continuous Sagnac loop including a first end 901 and a second end 902 of optical fiber. The optical radiation is injected into the two ends via the optical coupler 810. A suitable source driver 904 drives the optical source 900, which is controlled by a micro-controller 950. The first end 901 is connected to an optical fiber section 906 arranged in an approximate zigzag configuration within the sensor pad 120. At its other end, the optical fiber 906 is connected to the phase modulator 830, described with reference to FIG. 8. The phase modulator 830 is connected to a fiber delay coil 910, which is then connected to the depolarizer 870, described with reference to FIG. 8. The phase modulator 830 is driven by an oscillator 917 at a suitable frequency (approximately 30 kHz in one embodiment), and is used to add a high AC carrier frequency to the optical signal. The depolarizer 870 is connected to the second end 902 of the optical fiber. The depolarizer 870 is used to reduce optical signal fading resulting from polarization changes. The CW and CCW beams exit the Sagnac loop from the coupler 810, and are supplied via an optical fiber 913 to a photo detector 915, which is arranged to detect signal interference from the output of the coupler 810. The photo-detector 915 converts the optical signal to an electrical signal, which is applied to the amplifier 920, that in one embodiment includes a conventional DC-coupled transimpedance amplifier as the first stage. The interferometer generally produces a DC offset signal along with an AC signal if the splitter/coupler ratio is not precisely 50/50. To remove the DC offset signal, the output of the first stage of the amplifier 920 is AC-coupled to a second stage of the amplifier. The amplified signal is then passed on to a synchronous demodulator circuit 918 that uses a reference signal from the oscillator driver 917 to strip away the AC carrier frequency from the desired signal. The recovered signal is passed from synchronous demodulator 918 to the microprocessor based signal processing circuit 950.

In the speckle pattern prior art, to optimize detection sensitivity the output fiber 913 and the photo detector 915 are often arranged to receive only a fraction of the light from the fiber 913 containing the speckle pattern. In such a prior art case, the raw electrical signal from the photo-detector would represent the average intensity of the sample portion of the speckle pattern. In contrast, in one embodiment of the present invention, the output fiber 913 and the photo-detector 915 are arranged so that the photodetector collects the entire cone of light (i.e. all the energy) emitting from the fiber 913 rather than just a portion. If the entire cone of light is not collected, it would degrade the performance as a result of reduced signal to noise ratio. By collecting the entire light cone and tracking the phase of the modulated frequency via the synchronous demodulator, it is possible to achieve a very high signal to noise ratio.

Signal processing techniques, which can be accomplished by various approaches known to those skilled in the art, are employed to separate the signals from the synchronous demodulator 918 into heart rate, respiration and movement components. In one such signal processing technique, each component is analyzed to determine whether or not it falls within acceptable boundaries. The acceptable boundaries are thresholds that can be pre-programmed into the processor depending on the specifics of the patient being monitored. The results of the analyses of each component are output in a suitable manner, such as by display on a local graphical monitor 960. The display can range from a simple numeric readout of the present rate or be as involved as an LCD, LED bar graphs or oscilloscope-type displays of the signal level vs. time, for example. A user input interface 956 is used to program the microprocessor for the type of local display desired. If any of the monitored parameters go outside of the preset threshold boundaries, the micro-controller activates one or more local alarms 962.

The system shown in FIG. 9A provides remote signal outputs also. The microprocessor-based signal processing circuit 950 interfaces to an RF transmitter 964 and receiver 982 that provide communication with a remotely located readout unit 954, shown in FIG. 9B that includes a micro controller 972 connected to a RF receiver 970 and an RF transmitter 980. The remotely located readout unit 954, its operation and communication with RF Transmitter 964 and RF Receiver 982, as well as alternatives to the use of RF, discussed herein apply equally to all embodiments of the invention including the Alternative Embodiments discussed in detail below. In addition to the interferometer signal, the signal processor 950 may also monitor and report on the inputs of various auxiliary sensors 930 such as a microphone, thermometer, etc. to the remote unit. In response thereto, the micro-controller 972 located in the remote unit 954 generates signals supplied to an LCD display 974, an alarm function 978 such as a buzzer or vibrator. The signals from a micro-controller may also be supplied to a voice chip that announces the alarm condition via a speaker 979. Alternatively, chart recorders or computerized data collection and display systems may be used to record any of the signals both locally or remotely via modems or via other communication systems.

The communication link between the sensor pad 120 and the auxiliary sensors 930 (via the signal processor 950) to the remote unit 954 that is shown as RF in FIG. 9A can alternatively utilize infrared, AC power line carrier current, phone line, direct wire, optical, and etc. Also, many types of modulation could be used, such as AM, FM, FSK Spread Spectrum, Time Division Multiple Access (TDMA), Code Division Multiple Access (CDMA) and others. In order to provide bi-directional communication and implement a system for fail-safe handshaking to guarantee the integrity of the communications link, the RF transmitter 980, connected to the micro controller 972 of the remote unit 954, transmits to a second receiver 982 that is connected to the micro controller 950 of the electro-optic unit. For example, the micro-controller in the signal processor 950 can periodically send a message to the remote micro controller 972 and receive a handshake message via the return link from the remote transmitter 980 and the base unit receiver 982. In one embodiment, if the remote controller does not receive a communication in a pre-determined time, it can set off an alarm to notify the user that communication has stopped.

Under some circumstances for battery-operated systems, pulsing the optical source at frequencies much higher than the phase modulator frequency may extend the battery life. For example, if the phase modulator frequency is 30 kHz, the source may be modulated at 500 kHz with a 5–10% duty cycle. Care should be used in selecting the optical source modulation frequency to minimize signal degradation. Modulating the optical source may also be helpful to increase the signal over noise ratio, especially when the optical path losses are large and the detection sensitivity low resulting in marginal signal over noise ratio. For example, a marginal signal over noise ratio may occur when the optical source cannot be driven any harder in CW mode to overcome the optical path losses and detector sensitivity. In such a case, the optical source power may be pulsed in order to increase power in proportion to a reduction in duty cycle. The micro controller-based signal processing circuit 950 may be used to drive the optical source 900 with a narrow pulse width via the driver 904.

The remote unit 954 can comprise many different embodiments and configurations. In one embodiment, the visual and audio signals are displayed on the remote unit. An alarm is triggered upon any of the following events: the infant is not in the crib, system or fiber failure, absence of physical movement, absence of respiration or absence of heart beat, abnormal respiration, abnormal heart beat or any combination thereof. The alarm system may be designed so that it is not triggered by electrical noise or presence of acousto-mechanical noise. For example, this system could be implemented as an infant monitor that indicates his/her well being by providing heart beat, respiration and body movement or a combination thereof even when the infant is sleeping. Additionally the microphone sensor when integrated into the e-o unit or in the pad can detect and transmit normal sounds of the infant, especially when the infant is awake and moving around in the crib. The remotely located unit integrated with the speaker and the alarm provides the display with actual numbers and flashing indicators of the respiration, cardiac activity, body movement, cry/voice signals and monitor status. The bi-directional fail-safe communication system is used to maintain contact between the sensor system and a remote unit carried by the guardian, parent or caregiver.

In another embodiment, the optical source 900, photo-detector 915, and the associated circuitry such as preamplifier, filters and signal processing electronics shown in FIG. 9A may be situated in a single electro-optic unit. The sensor pad 120 and the electro-optic unit may be remotely located from each other by means of an inter-connect fiber cable. The light from the source located in the electro-optic unit is transported to and from the pad via a two fiber inter-connect duplex cable. The entire system excluding the sensor pad 120 can then be situated in one remote location with the caregiver, thereby precluding the need for a communication link.

Signal Processing and Separation of Signals

Many forms of signal processing can be utilized for the separation and conversion of the analog signals into digital signals that subsequently can be analyzed and displayed in various ways. A low cost approach suitable for in-home application is to use multi-pole filters, including a low pass filter and a high pass filter in the signal processing circuit 950 for the separation of movement from heart rate and breathing, and then using an A/D converter at the analog input of a single chip micro-controller to perform the analog to digital conversion. Once digitized, the rate can be calculated by the microcontroller in the circuit 950. The low pass filter separates the heart rate and breathing signal from the physical movement signal because these are lower in frequency compared to the movement signal. Therefore they can be easily processed by a low cost one-chip micro-controller where preset thresholds provide this functionality. Because in home environment, the movement signal is used to detect infant activity, it does not require highly accurate processing. The high pass filter is adequate to allow separation of the movement signal from the other two signals. On this channel, thresholds limits can be monitored using an analog integrator and comparator.

Figure 10:
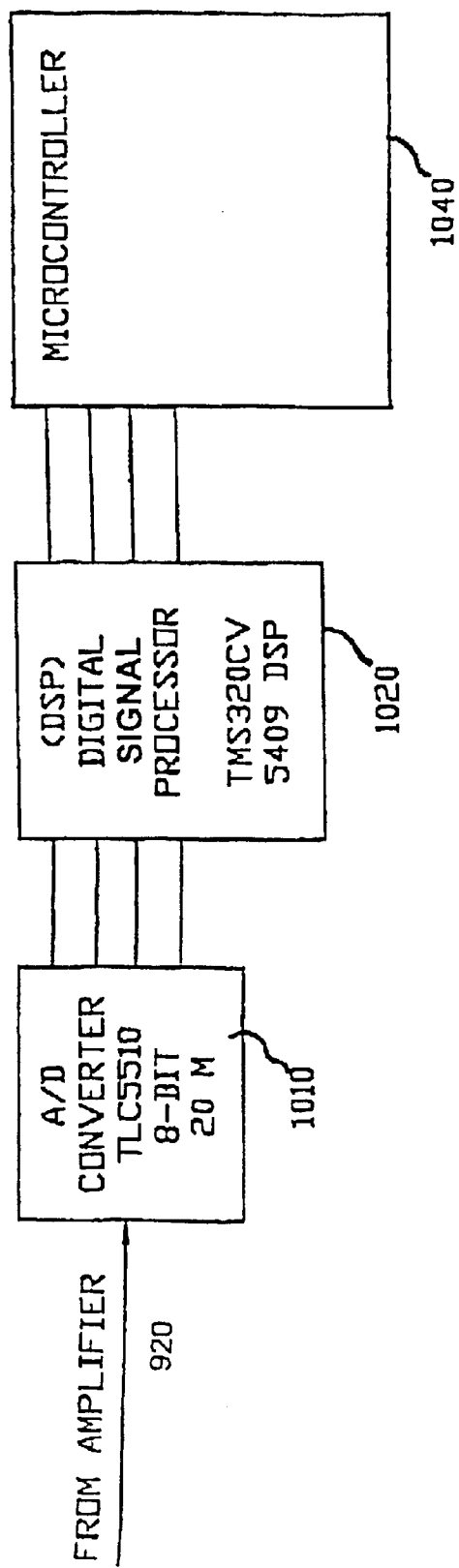
FIG. 10 is an alternative embodiment of a signal processor including digital processing circuitry suitable for uses such as where individual signals must be separated in the presence of physical movement.

Reference is now made to FIG. 10, which is a block diagram of an alternative embodiment of the micro controller-based signal processing circuit 950 that includes digital processing circuitry suitable for applications where reliable signal separation of the individual signals is required. For example, in hospital environment it is necessary to separate the heart beat signal from the respiration signal in the presence of the physical movement to better predict the onset of apenic event. The digital signal processing circuitry, such as shown in FIG. 10 can eliminate the need for the multi-pole filters and can provide high performance separation of the individual signals. In the embodiment shown in FIG. 10, the output from the amplifier 920 is supplied to the DSP processing circuit that comprises the A/D converter 1010, such as an 8-bit or 16-bit, 20 million sample per second A/D converter available from Texas Instruments (TLC5510). The digitized output is then supplied to the DSP circuit 1020 such as a DSP available from Texas Instruments (TMS320CV5409) although many other DSPs could also be used. The DSP 1020 provides a parallel input to a micro controller 1040. The DSP includes routines that perform the multi-pole filtering and threshold functions. The micro controller 1040 can then do the counting for the display of the rate information.

The DSP 1020 may include algorithms to account for a variety of effects and signal processing problems. For example, the algorithms may be designed to reliably detect and isolate the heart beat and respiration signals in presence of patient's physical movement when such noise is present over an approximate period of about three seconds (which is a low end for infant apnea alarm delay setting). Physical movement induced noise is generated when an arm or a leg or body of a patient rubs the pad. Because the physical movement noise signal amplitude is generally much greater than the respiration or the cardiac activity signals, it may result in data "washout" over the signal tracking period. If the noise tracking period is selected to be about three seconds, it will introduce a data latency of about three seconds in the heart and respiration signals. This may be reasonable provided the algorithms can track signals from the next cycle while displaying signals from the previous cycle. Pattern recognition techniques would allow separation of the heart signal from the respiration. However, if the physical movement noise period exceeds three seconds, the signal tracking period may be increased. The maximum tracking period may be limited to less than seventeen seconds based on upper end of apnea alarm delay setting of twenty seconds. Under such conditions, the data latency will be seventeen seconds, which must return to three seconds once the apnea event has passed. Alternatively, other advanced signal processing techniques such as auto time correlation, fast Fourier transforms, artificial intelligence, neural networks, fuzzy logic, and others may be implemented to separate the heart from respiration signals in presence of the physical movement noise signal.

Additional features of the algorithms may be to separate an infant's low heart rate from increased respiration rate. Under some conditions these two rates may be identical, resulting in false alarms. Separation may be accomplished by sampling higher frequency components associated with the heartbeat, which are generally absent in respiration signal. For example, the low heart rate (bradycardia) in infants ranges from 40 beats per minute (bpm) to 130 bpm, which can overlap with the typical respiration rate ranges from 1 breath per minute (bpm) to 99 bpm. Similarly, in adults the low heart rate is 30 to 100 bpm which somewhat can overlap with 15 to 30 breaths per minute.

The system algorithms may be designed to include variable alarm setting capability. For example, because the high heart rate (tachycardia), in infants ranges from 150 to 300 bpm whereas in adults it is 100 to 250 bpm, the heart alarm delay in each case may be adjusted from about three beats to seven beats. In a similar way, the apnea event alarm delay setting may be made variable and set to 3 to 40 seconds for infants (20 seconds is typical) and 10 to 25 seconds for adults.

Similarly, the algorithms may be designed to identify shallow respiration rates from no respiration that causes reduction of heart rate (bradycardia). Many other conditions may be programmed providing reliable monitoring while achieving reduced false alarm rates compared to previous systems.

Sample Test Data

Figure 11:
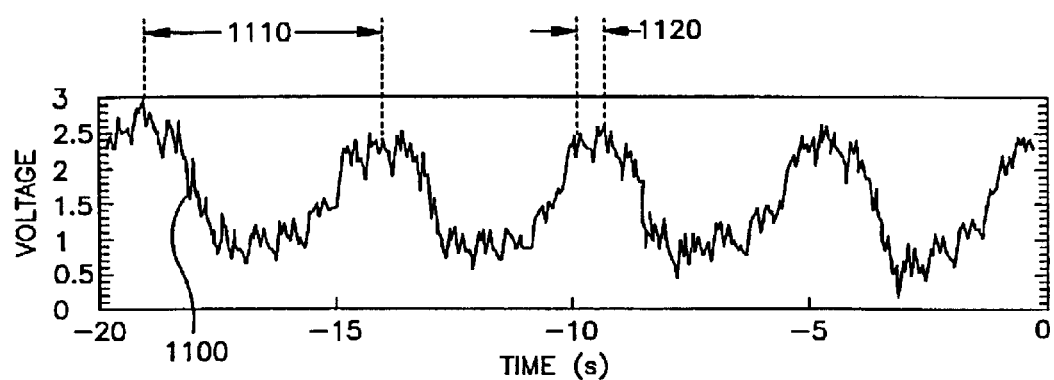
FIG. 11 is a graph of amplitude vs. time, showing experimental data in one embodiment in which heartbeat and respiration of a normal infant are output in the form of a combined signal.
Figure 12:
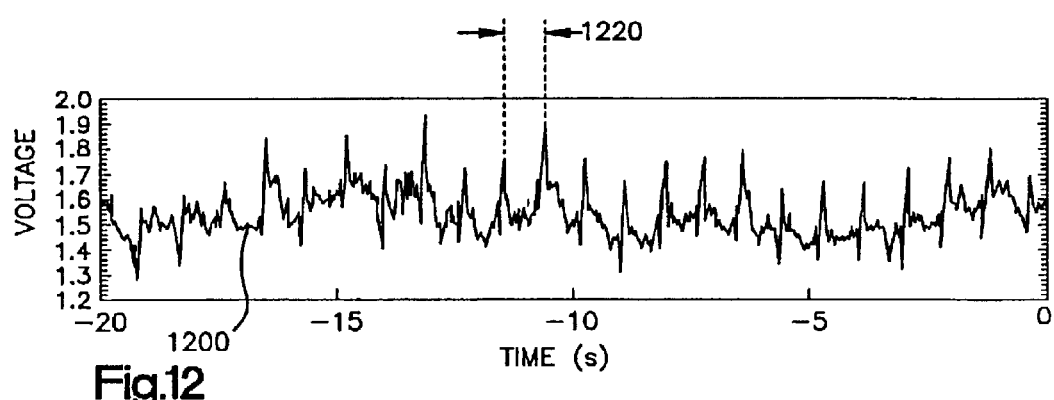
FIG. 12 is a graph of amplitude vs. time, showing data in an embodiment in which heartbeat and respiration of a normal infant are output in the form of a combined signal.

FIG. 11 is a graph of experimental data over a period of about twenty seconds of a normal infant, obtained using one interferometric monitor as described herein, in an implementation in which the heartbeat and respiration are output in the form of a combined signal 1100. The horizontal axis shows time, and vertical axis shows amplitude of the combined signal. In the graph of FIG. 11, it can be seen that the weaker but higher frequency heartbeat signal is superimposed upon the stronger, lower-frequency respiration signal. Particularly, the lower-frequency respiration signal in FIG. 11 has a period shown at 1110 of approximately five seconds, while the higher-frequency heart beat has a period shown at 1120 of less than about one second, which is normal for this patient.

FIG. 12 is a graph of experimental data over a period of about twenty seconds of the same infant, obtained using the same interferometer monitor as described herein but with a different sensor pad configuration than in FIG. 11, in an implementation in which the heart and respiration signals are output in the form of a combined signal 1200 in which the heart signal is better defined than the respiration signal. As in FIG. 11, the horizontal axis shows time, and vertical axis shows amplitude of the combined signal. In the graph of FIG. 12, it can be seen that the higher frequency heart signal has much larger amplitude than in FIG. 11, which results from adjusting certain parameters in the pad and optical fiber to strengthen the coupling of the higher-frequency acousto-mechanical signals into the optical fiber. The higher-frequency heart signal has a period shown at 1120 of less than about one second, which is normal for this patient, while the lower-frequency respiration signal has a period of approximately 5 seconds, which is detectable but difficult to measure precisely compared to FIG. 11 sensor configuration.

Alternative Embodiments

It will be appreciated by those skilled in the art, in view of these teachings, that the following alternative embodiments may be implemented without deviating from the spirit or scope of the invention.

1. MRI Environment Embodiment

Because the electrical activity of the myocardial is unreliable in the MRI, we can exploit the mechanical activity of the myocardium in this aspect of the invention. This is because the mechanical activity of the myocardium is unaffected by the static/varying magnetic fields and the RF, unlike measurement using the EKG. Additionally, because fiber optic sensors are used in the present invention to detect the acousto-mechanical activity of the myocardium, high confidence can be established regarding the reliability of the optical data since fiber optic sensors are essentially immune to the MRI environment. Therefore, those skilled in the art could rely more on the fiber optic sensors than the EKG in detecting different vital conditions in the MRI. The mechanical activity obtained using the inventive fiber optic sensor (FIG. 13) is similar to the EKG vital sign information.

This invention uses interferometric based fiber optic sensors of the present invention in monitoring the vital signs of patients that are either sedated or present a high risk of having heart attacks during the MRI. In addition to their completely passive characteristics, they are non-invasive providing ease of use without posing any bio-chemical threats. They are small in size similar to graphite electrodes, can be configured to monitor local or distributed areas depending on if they are configured as optrodes, mattress pads or wearable jackets. Because the leads are all fiber optic, they do not have to be shielded and long extensions may be used without large signal losses. They provide high performance because they detect movements smaller than the wavelength of light due to their interferometric characteristics. These properties are used in monitoring the key vital signs and addressing the above listed MRI problems.

1.1 Description of Sensor System:

In the MRI environment, the fiber optic sensor pad may be placed in contact with the body, as shown in FIG. 1, except for an intervening layer of fabric or other protective material); to detect, in particular, the myocardium sounds (S1, S2, S3 and S4) and the respiration rates simultaneously.

Figure 13A:
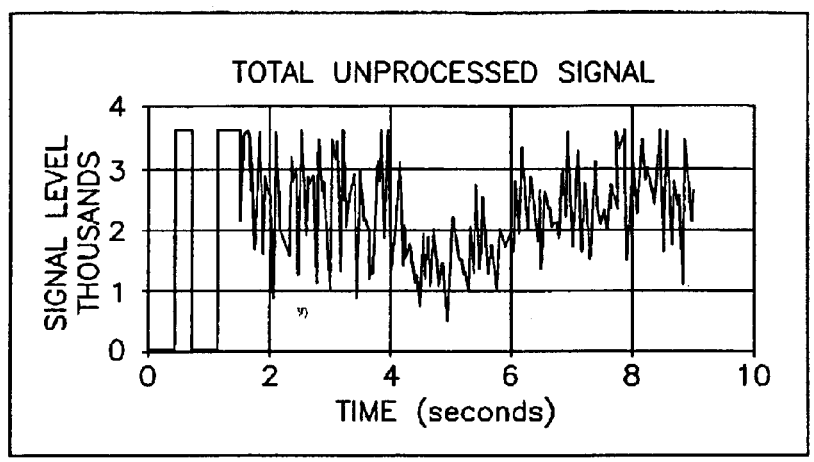
FIGS. 13A–C shows vital sign waveforms obtained via the fiber optic interferometric sensor of the present invention.
Figure 13B:
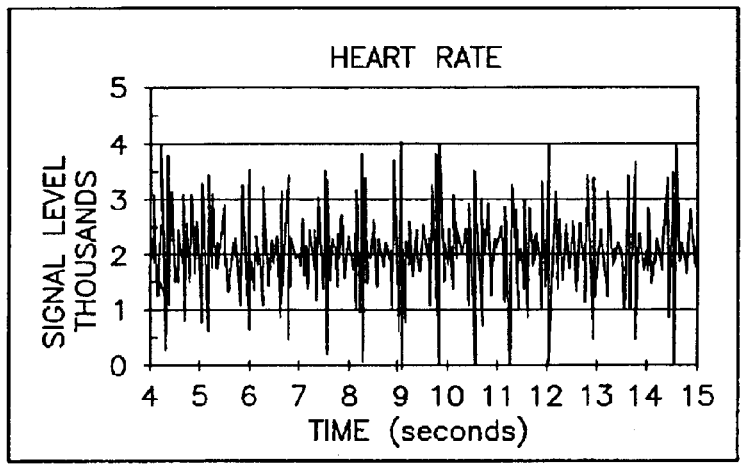
Figure 13C:
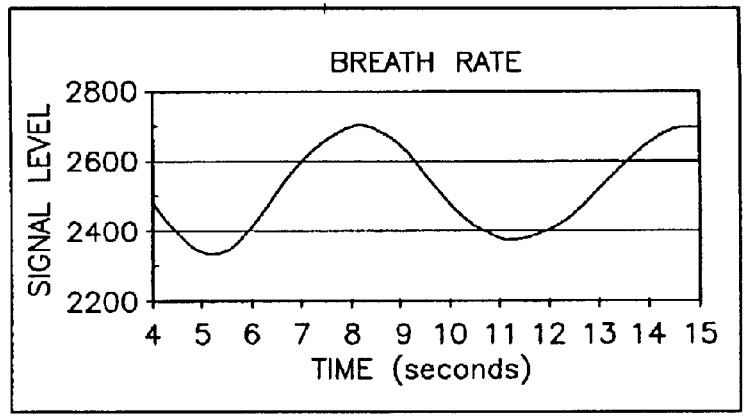

Using the fiber optic sensor of the present invention, FIG. 13 shows the separated heart rate and the respiration rates of a patient, which are two vital sign parameters that must be detected reliably during MRI scanning.

In one embodiment of the sensor design, a single or plurality of the inventive sensors may be used for listening to both the normal and abnormal heart sounds (S1, S2, S3 and S4) in addition to detecting the respiration rate. Because the first heart sound represents the closure of both the mitral and tricuspid valves and also represents the initiation of ventricular contraction or systole, it is generated within tens of milli-seconds after the EKG's QRS complex and can be used to determine the heart rate. In the same way, the S2 sound represents the closure of both the aortic and pulmonary valves and represents also the initiation of the ventricular relaxation or diastole occurring at the same time as the T wave in the EKG. This correlation of the heart sounds and the EKG waveforms is well known as shown in the figure from the literature entitled "Phonocardiography: Measurement of Heart Sounds," which is incorporated herein by reference in its entirety. Because the S1 sound is strong, it can be used to measure the heart rate more accurately than by the R spike of EKG. This is because in the EKG, the presence of R spike artifacts can corrupt the count, which is not the case when counting S1 peaks in the optical channel. The S1 signal cannot be generated in the fiber optic sensor output unless it is real. On the other hand, absence of S1 sound or abnormal sound would suggest heart problems. In such a case, the patient may be removed from the MRI, an EKG administered without the magnetic fields along with life saving CPR etc.

Figure 14A:
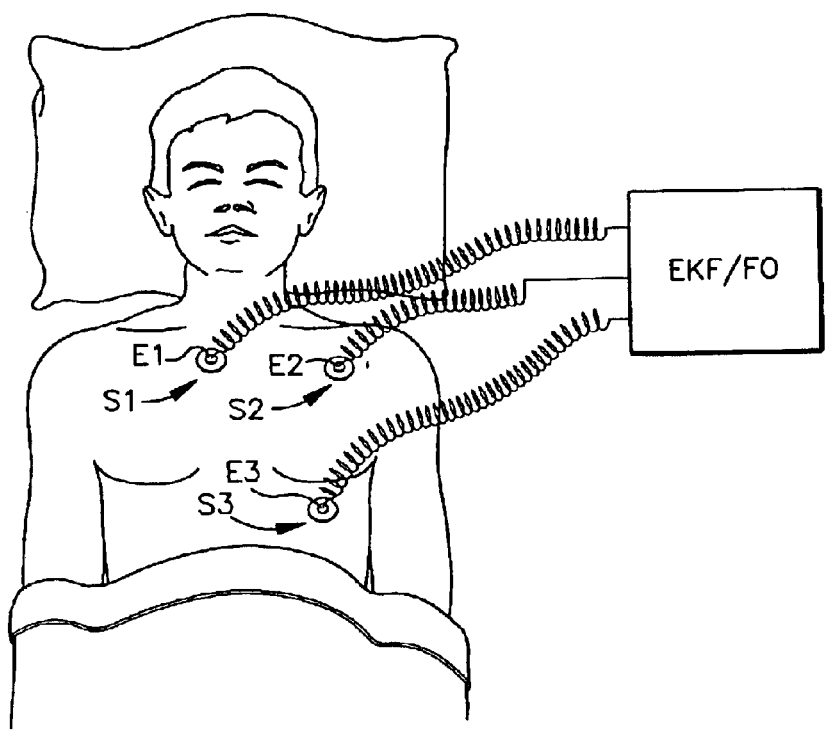
FIG. 14a shows a 3 lead EKG hookup with Fiber Optic Sensors (Optrodes)
Figure 14B:
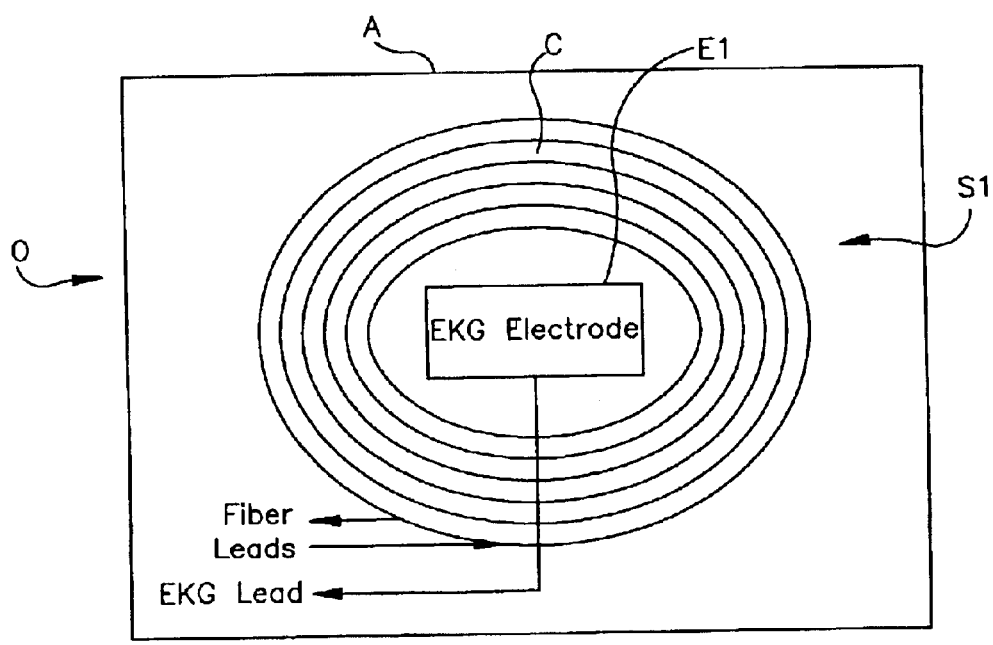
FIG. 14b shows typical EKG electrodes contained with the inventive fiber optic sensor in a patch or cuff.

1.2 Optrodes:

In another embodiment of the sensor design, multiple optical sensors S1, S2, S3 may be combined with graphite EKG electrodes E1, E2, E3 (one of the combined units, called an optrode O being shown in FIG. 14*b* comprising fiber leads extending from a coil C of optical fiber and an EKG lead extending from the EKG electrode), affixed via a patch or cuff A to the patient's chest around the apex, atria and ventricles and extending to an EKG/fiber optic unit constructed in a manner that would be apparent to one skilled in the art in view of this disclosure, to correct the corrupted EKG data. A microprocessor based counter, recorder and signal correction algorithms may facilitate the correction process. The setup is generally shown in FIG. 14.

In this embodiment, the output signals from both the optical sensor and EKG electrodes are correlated and processed to eliminate the unwanted R spikes while correcting the elevated ST and T waveforms. Because R spikes and the elevation of the ST segment and the T wave in the EKG can be generated from the varying MRI magnetic fields as artifacts, these do not appear in the optical S1 and S2 signals. Different schemes to process these signals may be used such as fast Fourier transforms or time correlation filtering techniques for correcting the corrupted EKG signals that may otherwise pose life threatening effects.

1.3 Central Monitoring Station Readout Interface

At the central monitoring station, information about the patient is generated using both the vital signs that have been processed using a signal processor. This information can be provided as follows: a graphical display of the breath rate; a numeric display of the breath rate; a graphical display of the heart rate or corrected heart rate; a numeric display of the heart rate.

The following series of alarms may be communicated, in the form of a text message, a flashing light, an audible signal, or any combination of these:

Alarm #1 when the breath rate is faster or slower than a preset threshold value;

Alarm #2 when the heart rate is faster or slower than a preset threshold value;

Alarm #3 when heart rate signal indicates onset of a heart condition.

All or any portion of the above information set may be displayed/output at either the local readout or remote readout. Specific installations may differ in the configuration of the readouts. The most complete embodiment will output the complete information set at both the local and remote readouts.

1.4 Communication Link:

Because the remote readout interface at the central station may be several hundred feet from the signal processor, some form of communication channel to transfer the information is required. The heart and breath rate signals of the Fiber Optic Monitor along with the EKG signals may be transported by a standard BUS protocol for example on an RS485 or CAN BUS that is hardwired to the central monitoring station from the local readout.

2. Confined Care Facility Embodiment

This aspect of the invention is intended to serve that class of patients (usually but not exclusively elderly) who are mostly confined to their beds or rooms such as at elderly care facilities, nursing homes, hospice and convalescent homes, sanatoriums or insane asylums, and centers for recovery from drug and alcohol abuse (Confined Care Facilities). These patients require significant or constant oversight to monitor their well-being and whereabouts within the facilities usually over the long term. Ideally, a nurse or other caregiver would attend the patient's bedside at all times. However, it is generally impractical and uneconomical to provide this level of care at these facilities. Typically, a few staff personnel serve many patients periodically checking on the status of individual patients. Because the caregivers/staff are not constantly aware of the condition of each patient, serious problems can develop. A patient may leave their bed, either intentionally or accidentally. Even if intentional, the patient may take a fall or become disoriented without being able to timely press the emergency button to seek help. Dementia patients wander off from their rooms or the facility altogether making it difficult for the staff to determine their whereabouts. With only periodic checks by the staff and no capability to determine their whereabouts, the patient may be exposed to extended periods of physical and/or mental distress before being located and rendered help to prevent untimely deaths.

2.1. Description of Sensor System

This embodiment of the invention employs a combination of the passive inventive fiber-optic interferometry system which is described in detail herein above (e.g., FIGS. 1, 9A, 9B and 10) and an RF or IR transmitter cuff that is issued to the patient on checking into the facility (FIG. 15). The fiber optic system continuously monitors the patient's vital signs (including heart rate and breath rate) and provides immediate notification to the staff in case either rate goes outside of prescribed bounds, or in case the patient leaves the bed and the rate signals are lost altogether, whereas, for example, the RF transmitter emits a patient Identification (ID) code that is picked up by RF receivers installed in the room, bathroom and hallways to determine his/her whereabouts.

As shown in FIG. 15 directed to a general description of this embodiment, the sensor pad 1410 comprises a coil or serpentine shape of optical fiber that responds to acousto-mechanical movements of the patient. It is contained by a pad that lies on the patient's bed placed under the bed-sheets as shown above (e.g., FIGS. 2 and 9A). No connections (wires, fibers, or tubes) to the patient are necessary. The patient merely lies on the bed and the sensor pad responds to the micro-movements caused by the patient's heartbeat and breathing. Two optical fibers packaged in a single cable emerge from the sensing pad and connect to the Fiber Optic Signal Conditioning Box 1412. The box includes the following (such as shown in FIG. 1): a light source that sends light through the fiber coil in the sensing pad; a detector that converts the light that has traveled through the sensing coil into an electrical signal; a processor that extracts the breath rate and heart rate from the modulation of the detectors signal; an interface communication module located in the signal conditioning box that sends the results to the local and/or central/monitoring station 1414 to provide numeric readouts and alarms; the vital sign signals may be transmitted over exiting power lines, wireless radio link or new phone lines, cable lines, local area network lines that may be fiber optic or copper or other suitable manner.

A battery operated short range RF or IR transmitter cuff 1416 emits the patients ID periodically at preset intervals. This cuff is placed on the patient's wrist or leg, for example. The code is unique and is emitted in serial time segments in such a way that there are no message collisions between the IDs of various patients within the facility resulting in data washout at the receiver. Short range RF or IR Receivers 1418 located within the bedroom, bathroom and hallways pick up these unique signals. The receivers perform the following functions: they detect and process each patient's ID code; an interface communication module in the receiver transmits the message consisting of the processed ID codes and location of each patient to the central monitoring station; the messages may be transmitted over exiting power lines, wireless radio link or new phone lines, cable lines, local area network lines that may be fiber optic or copper.

2.2. Central Monitoring Station Readout Interface

At the central monitoring station 1414, information about the patient is generated using both the vital sign and the RF signals that have been processed using a signal processor. This information for each patient can be provided as follows: a graphical display of the breath rate; a numeric display of the breath rate; a graphical display of the heart rate; a numeric display of the heart rate; a numeric display of the patient's location within the facility or visual display such as a point representing in real time the location of the patient on a graphical map of the facility.

The following series of alarms may be communicated, in the form of a text message, a flashing light, an audible signal, or any combination of these:

Alarm #1 when the breath rate is faster or slower than a preset threshold value;

Alarm #2 when the heart rate is faster or slower than a preset threshold value;

Alarm #3 when no breath or heart rate signal is available because the patient has left the bed or wandered off and not returned to the bedroom after a preset time duration has elapsed.

Alarm #4 when no breath or heart rate signal is available because the patient has left the bed and has not moved from a particular location after preset time duration has elapsed.

All or any portion of the above information set may be displayed/output at either the local or the remote Readout Interface. The location of the local readout interface may be in the patient's room. Specific installations may differ in the configuration of the readouts. The most complete (and expensive) embodiment will output the complete information set at both the local and remote readouts. For economy and to match the specific needs of a given installation, the information output may be shared between the local and remote readouts. In the simplest configuration there will be no local readout and the remote readout will only provide the Alarms.

2.3 Communication Link:

Two communication links are established within the Confined Care Facility:

1. The heart and breath rate outputs of the Fiber Optic Monitor are communicated to the central monitoring station from the local readout, which is housed within the same enclosure as the signal processor. The remote readout interface at the central station however, may be several hundred feet from the signal processor, creating a need for some form of communication channel to transfer the information.

2. The RF or IR Receiver output that detects the location of the patient within the room, bathroom or hallways is provided to the central station.

There are several options for the two communication channels and the choice is determined by the specifics (including economics) of the particular installation. The primary options are: through existing or newly installed phone or computer network lines, which may be either copper or optical fiber, over existing power (110VAC) lines utilizing for example PLC E-Modem 101 at archnetco.com or Philips TDA5051A power line modem at www.michat.com, via a wireless (radio) link.

Usually multiple patients will be monitored by a single remote readout station located at the staff desk. For both of the approaches that transfer the information over wires/fibers, there exist standard communication protocols such as RS485, and Ethernet that allow a single receiving station to monitor multiple sources.

Although there are currently no established standards for the wireless case, multiple transmitters can be monitored by a single station using existing equipment. To avoid message "collisions" (simultaneous arrival at the central readout station of messages from two or more patient monitors) the preferred embodiment will employ a polling protocol. The individual patient monitors will only transmit their information to the central readout station when requested by a message from the central readout. The request message will be encoded with a name/number that is different for each readout channel, i.e. the request for information message will consist of the request plus an ID that specifies which channel/patient should respond. The central readout station will scan through each channel in turn; requesting, then receiving and displaying/outputting the requested message. Even with an extreme case of 100 patient channels reporting to a single central monitoring station, the information exchange is fast enough that every patient can be reported on every few seconds.

3. In Hospital Use Embodiment

This embodiment employs the all-passive interferometric fiber-optic sensor described above in this patent application for in-hospital use. Because the fiber optic sensor responds to acousto-mechanical signals, it can be used to continuously and non-invasively monitor patient's blood pressure, heart and respiratory rates. The present discussion focuses on the inventive fiber optic monitor in measuring two of the three functions; namely blood pressure and heart rate. The system (FIG. 16) consists of the following: a cuff 1420 with integrated fiber optic sensor; controls and signal conditioning unit 1422; central monitoring station 1424, and communication link 1426.

3.1 Description of Sensor System:

A cuff 1420 is used to measure both the blood pressure and heart rate non-invasively and continuously. The cuff may be inflated or deflated using an air pump 1428 that is located outside the cuff in the controls unit to achieve a proper preload (defined as the hold down pressure). Alternatively, the fiber optic integrated cuff tension may be adjusted mechanically to achieve the proper preload. The fiber optic sensor 1430, which is configured into a flat ribbon, is integrated within the cuff in such a way that they can be wrapped lightly around the patient's arm or leg with the proper preload that is required to detect pulsation of the arterial wall. Because the fiber optic sensor is extremely sensitive, a minimal hold down pressure is sufficient to achieve good coupling between the sensor and the arterial wall. Applying the minimal hold down pressure ensures comfort to the patient for monitoring BP and heart rate continuously over extended periods. High sensitivity, distributed area sensing and immunity to EMI, RFI, etc. are some of the key advantages offered by the fiber optic sensor of this aspect of the present invention.

The cuff is designed, for example, to be approximately 3 inches wide by 10 inches long containing the fiber optic sensor ribbon. It is configured in such a way that when the sensor cuff is wrapped around the radial artery for example, a total fiber sensing length of approximately one meter is in contact with approximately 50 mm×5 mm area of the artery. Although this sensor fiber length per area advantageously increases sensitivity, those skilled in the art will appreciate upon reading this disclosure, other fiber lengths per area may be suitably used. Multiple strands of a continuous single fiber configured into the ribbon are tightly packed for quick placement of the cuff around the arterial wall. No special alignment of the sensor cuff with the arterial wall is required because the sensor used is intrinsically a "distributed area sensor". Optimizing the sensor dimensions for a given cuff size minimizes the fiber sensor contact area outside of the arterial wall resulting in reduction of patient generated noise. Additionally, time correlation algorithms referenced to the pulse rate are used to further reduce movement-induced patient noise. Air-lines or an air ballast 1432 may be employed for inflating or deflating the cuff with integrated fiber optic sensor using a microprocessor 1434 driven servo control pump 1428 that is located in the controls unit. Alternatively, the system may also be configured using a separate air cuff located next to the elastic cuff with integrated fiber optic sensor. Also, because the fiber optic sensor input/output fiber optic lead lines 1436 run between the cuff and the controls unit, these are packaged along with the air-lines into a cable providing ease in handling, maneuvering and minimizing clutter.

The auscultatory/oscillometric method is implemented in the fiber optic sensor cuff to measure blood pressure. When the system is used, it first goes through a preprogrammed test sequence to set the hold down cuff pressure before being used in continuous mode for measuring BP. In the first step of the setup sequence, the cuff is inflated to occlude the blood flow while the fiber optic sensor looks for the presence of pulses. A safety design circuit is implemented to ensure that the pressure in the cuff does not exceed the maximum threshold pressure for a set interval (for example 250 mm Hg for a period of 10 seconds).

Following the blood flow occlusion step, the cuff pressure is released slowly while the pulse amplitude and rate are monitored/recorded. Releasing the cuff pressure in a controlled fashion returns the flow of blood reproducing the pulse (systolic pressure). At the instant the fiber optic sensor first detects the pulse, the pressure gage reading in the control unit is automatically recorded. This is the systolic pressure. Further reduction of the air cuff pressure in the $3^{rd}$ step increases the pulse amplitude followed by peaking after which the pulse amplitude goes down to an undetectable level. The pressure when the pulse is no longer detectable is called the diastolic pressure, which is also recorded automatically in the control unit.

The pulse rate as measured by the fiber optic sensor and the pressure gage readings recorded for the systolic and diastolic pressures are processed in near-real time. From this data, the optimum hold down pressure for the cuff is determined and applied for continuous monitoring. The correct hold down pressure provides the optimum fiber optic sensor signal for continuously monitoring the BP while ensuring comfort to the patient. Once the hold pressure is determined, it is actively controlled by the servo control pressure system in the control unit throughout its usage.

Figure 17:
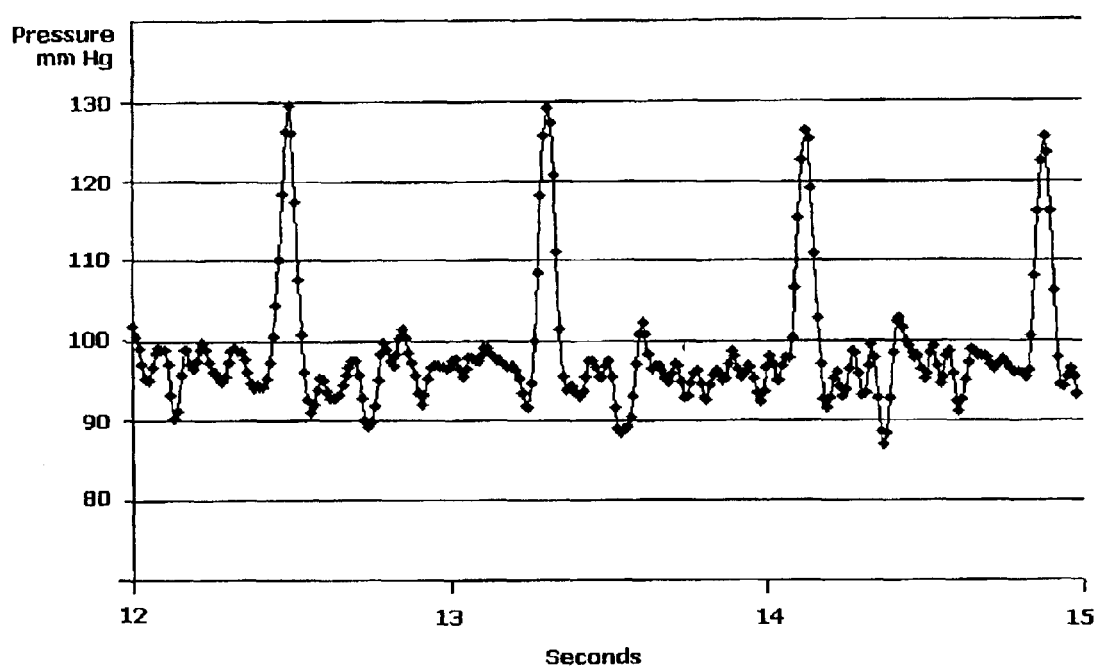
FIG. 17 is a graph showing continuous blood pressure measured at the brachial artery of the forearm using a surface fiber-optic sensor placed over the Antecubital Fossa.

In determining blood pressure, the fiber optic sensor detects the time-dependent transverse motion of the arterial wall. As blood pressure fluctuates with the cardiac cycle, the blood vessel's wall radius (R) enlarges and contracts according to a basic isotropic version of Hooke's law. The signal detected by the sensor represents the first derivative of motion of the wall (dR/dt). Assuming that dR/dt=K dP/dt, where dP is change in pressure in the artery, t is time, and K is an empirically determined biomechanical constant for the system (measured, for example, using the actual cuff pressure at initial calibration). Integration of ∫KdP/dt over a time interval therefore provides a measure of the intra-arterial pressure as a function of time. FIG. 17 shows an actual tracing of continuous blood pressure measured using this system.

3.2 NIBP Calibration

There are two types of calibration required for the non-invasive blood pressure (NIBP) system to operate over extended periods continuously while providing accurate data. These are calibration of the pressure gage; and calibration of the biomechanical constant, K, that relates the fiber sensor signal amplitude to the pressure determined by the pressure gage.

In the first case, the calibration of the cuff pressure is performed against a National Institute of Standards and Technology (NIST) traceable pressure sensor in the factory initially and then periodically thereafter. This calibration warrants that the BP pressure readings recorded and displayed are accurate. In the second case, the biomechanical constant, K, may require recalibration after extended periods of use. This may be due to the fact that either the blood pressure may have actually changed or for other reasons such as: changes in sensor orientation with the arterial wall; changes in skin tissue elasticity, arterial wall size, swelling, etc; variations in the hold down pressure.

The effect of the first two cases results in a slow drift in the fiber optic sensor signal output. Running the cuff step sequence periodically provides recalibration and compensation of the drift automatically. The microprocessor within the control unit automatically determines the calibration factor, K, after each calibration sequence and the result stored in the controls unit. This data is then used to compensate the signal drift resulting from these variations. The third case of hold down pressure variation is eliminated by maintaining the cuff pressure constant using the microprocessor driven servo control system.

3.3 Controls and Signal Conditioning Unit:

The Controls and Signal-Conditioning unit includes various elements one of which is an LED 1438 that sends light through an input fiber optic line 1436*a* into the sensor located in the sensing cuff. A detector 1440 converts the light returned from the sensor via a second fiber optic line 1436*b* into electrical signals. A servo control pressure system 1442 including the servo pump and pressure gage may be used to occlude blood flow for calibration or to regulate the hold down pressure in the air cuff. The microprocessor 1434 provides automatic calibration of the system, initiates the step sequence command to determine optimum hold down pressure, applies algorithms for noise minimization and drift control, conducts built in test, and provides safety pressure threshold limits, blood pressure and heart rate data storage, processing, and manipulation. The Controls and Signal-Conditioning unit provides local numeric and graphical displays and alarms 1444. A keypad 1446 is used through which a user can interface with the system for set up and calibration. A communication link module 1426 sends the data to the local 1444 and/or central monitoring station 1424 to provide numeric readouts and alarms. The link could be over existing power lines, a wireless radio, existing or new phone lines, cable lines, and local area network lines that may be fiber optic or copper.

3.4 Central Monitoring Station Readout Interface

At the central monitoring station 1424, information about each patient is recorded and reported to the staff. The following information as a minimum can be provided for each patient: a graphical display of the blood pressure vs. time; a numeric display of the current blood pressure reading; a graphical display of the heart rate; a numeric display of the heart rate.

The following series of alarms may be provided, which can be a text message, a flashing light, an audible signal, or any combination of these:

Alarm #1 when the blood pressure is higher or lower than preset threshold values;
Alarm #2 when the heart rate is faster or slower than preset threshold values;
Alarm #3 when the hold down pressure exceeds the threshold.

All or any portion of the above information set can be displayed/output at either the local or the remote Readout Interface. Specific installations will differ in the configuration of the readouts. The most complete (and expensive) embodiment will output the complete information set at both the local and remote readouts. For the purposes of economy and matching the specific needs of a given installation, the information output can be shared between the local and remote readouts. In the simplest configuration there will be no local readout and the remote readout will only provide the Alarms.

3.5 Communication Link:

Multiple patients monitored by a single remote readout station may be located at the staff desk typically within the same room. Results from the individual patients can be communicated to the central station using standard communication protocols such as RS485, and Ethernet that allow a single receiving station to monitor multiple sources. The communication can be over copper wires, optical fibers or wireless.

Those skilled in the art would appreciate that modifications and variations may be made to the invention as disclosed and shown herein without departing from the scope of the invention as defined in the following claims.

What is claimed is:

1. A method of detecting vital signs of a patient exposed to nuclear magnetic resonance imaging, comprising:
    providing optical fiber proximate to a patient exposed to a nuclear magnetic resonance imaging environment, said optical fiber comprising a first optical path and a second optical path;
    coupling optical radiation into an input of said first optical path and an input of said second optical path;
    coupling acousto-mechanical signals indicative of vital signs generated by said patient into said optical fiber to modulate a physical parameter of said optical fiber responsive to said acousto-mechanical signals;
    creating interference of optical radiation emitted from an output of said first optical path and an output of said second optical path;
    detecting time variations of said interference and providing a time-varying electrical signal responsive thereto; and
    signal processing said time-varying electrical signal to provide one or more output signals indicative of said vital signs.

2. The method of claim 1 comprising providing said one or more output signals indicative of said vital signs during administration of anesthesia to said patient while exposed to the nuclear magnetic resonance imaging environment.

3. The method of claim 1 wherein said vital signs comprise at least one of heart and respiration rates.

4. The method of claim 1 wherein said acousto-mechanical signals correspond to myocardial sounds selected from the group consisting of S1, S2, S3 and S4 myocardial sounds and combinations thereof.

5. The method of claim 1 further comprising monitoring heart electrical activities using an electrocardiogram.

6. The method of claim 1 comprising providing an electrocardiogram waveform based on output signals from an electrocardiogram used on said patient exposed to the nuclear magnetic resonance imaging environment, and correlating said one or more output signals indicative of said vital signs and said output signals from said electrocardiogram effective to supplement or correct said electrocardiogram waveform.

7. The method of claim 1 comprising providing an electrocardiogram waveform based on output signals from an electrocardiogram used on said patient exposed to the nuclear magnetic resonance imaging environment, correlating said one or more output signals indicative of said vital signs and said output signals from said electrocardiogram effective to supplement or correct said electrocardiogram waveform, and using said corrected electrocardiogram waveform to improve electrocardiogram reliability in detecting heart condition information comprising at least one of rate, rhythm, axis, hypertrophy and infarction.

8. The method of claim 1 further comprising monitoring heart sounds using a listening or recording device.

9. The method of claim 1 further comprising measuring said vital signs using a technique selected from the group consisting of pulse Oximetry, respiration measurements using capnograph or end-tidal volume $CO_2$, blood pressure measurement, body temperature measurement, and combinations thereof.

10. The method of claim 1 comprising a mattress pad or a jacket that contains said optical fiber.

11. The method of claim 1 wherein a first optical fiber comprises said first optical path and a second optical fiber comprises said second optical path.

12. The method of claim 1 wherein a single optical fiber comprises both said first optical path and said second optical path.

13. A method of detecting vital signs of a patient, comprising:

providing optical fiber proximate to a patient comprising a first optical path and a second optical path;

coupling optical radiation into an input of said first optical path and an input of said second optical path;

coupling acousto-mechanical signals indicative of vital signs generated by said patient into said optical fiber to modulate a physical parameter of said optical fiber responsive to said acousto-mechanical signals;

creating interference of optical radiation emitted from an output of said first optical path and an output of said second optical path;

detecting time variations of said interference and providing a time-varying electrical signal responsive thereto; and signal processing said time-varying electrical signal to provide one or more output signals indicative of said vital signs.

14. The method of claim 13 wherein a first optical fiber comprises said first optical path and a second optical fiber comprises said second optical path.

15. The method of claim 13 wherein a single optical fiber comprises both said first optical path and said second optical path.

16. A fiber optic monitor for detecting vital signs in a patient comprising:

optical fiber comprising a first optical path and a second optical path, said optical fiber being adapted to be situated proximate to a patient so that acousto-mechanical signals generated by said patient are coupled into said optical fiber effective to modulate a physical parameter of said optical fiber responsive to said acousto-mechanical signals;

optrodes for affixing at least a portion of said optical fiber to the patient;

an optical source coupled to supply optical radiation into an input of said first optical path and an input of said second optical path;

an optical system for creating optical interference from the optical radiation emitted from an output of said first optical path and an output of said second optical path;

a photo-detector arranged to sense an optical signal provided by time variations in said interference, said photo-detector providing a raw electrical signal responsive thereto;

a signal processor coupled to said photo-detector to process said raw electrical signal to provide one or more processed output signals indicative of vital signs of the patient; and an output system that communicates said one or more output signals.

17. The fiber optic monitor of claim 16 wherein said output signals are indicative of vital signs selected from the group consisting of heart rate, respiration, movement and combinations thereof.

18. The fiber optic monitor of claim 16 further comprising electrodes of electrocardiogram equipment adapted for use as a group with said optrodes of said fiber optic monitor.

19. A method of detecting vital signs of patient in a confined care facility in which the patient is confined to a bed or room during treatment or monitoring, comprising:

providing optical fiber proximate to the patient comprising a first optical path and a second optical path;

coupling optical radiation into an input of said first optical path and an input of said second optical path, coupling acousto-mechanical signals indicative of vital signs generated by said patient into said optical fiber to modulate a physical parameter of said optical fiber responsive to said acousto-mechanical signals;

creating interference of optical radiation emitted from an output of said first optical path and an output of said second optical path;

detecting time variations of said interference and providing a time-varying electrical signal responsive thereto;

signal processing said time-varying electrical signal to provide one or more output signals indicative of said vital signs; and communicating said output signals in a manner selected from the group consisting of: 1) as a local numerical or graphical readout near the patient, 2) over at least one of fiber optic lines, phone lines, power lines, local area network lines, and TV cable lines to a central monitoring station to produce a numerical or graphical readout, and the combination of 1) and 2).

20. The method of claim 19 wherein said vital signs include heart rate and respiration, comprising communicating an alarm if said output signals are outside of predetermined boundaries of said vital signs.

21. The method of claim 19 further comprising monitoring a location of said patient within the facility by transmitting an identification short range radio frequency signal from said patient to a radio frequency receiver, and transmitting an output of said radio frequency signal from said radio frequency receiver over at least one of fiber optic lines, phone lines, power lines, local area network lines, and TV cable lines, to a central monitoring station.

22. The method of claim 19 wherein said vital signs include heart rate and respiration, comprising communicating an alarm under conditions selected from the group consisting of:

1) breath rate is faster or slower than a preset threshold value of the breath rate, 2) heart rate is faster or slower than a preset threshold value of the heart rate, 3) no breath or heart rate signal is available because the patient has left the bed and not returned to the bedroom after a preset time duration has elapsed;

4) no breath or heart rate signal is available because the patient has left the bed and has not moved from a particular location after a preset time duration has elapsed, and combinations of 1) through 4).

23. The method of claim 19 comprising containing said optical fiber in one of a mattress pad and jacket vest operated by batteries.

24. A fiber optic monitor for detecting vital signs in a patient, comprising:

optical fiber comprising a first optical path and a second optical path, said optical fiber being adapted to be situated proximate to a patient so that acousto-mechanical signals generated by said patient are coupled into said optical fiber effective to modulate a physical parameter of said optical fiber responsive to said acousto-mechanical signals;

a casing containing at least a portion of said optical fiber and being adapted to be affixed to the patient, said casing being one of a cuff and a patch;

an optical source coupled to supply optical radiation into an input of said first optical path and an input of said second optical path;

an optical system for creating interference from the optical radiation emitted from an output of said first optical path and an output of said second optical path;

a photo-detector arranged to sense an optical signal provided by time variations in said interference, said photo-detector providing a raw electrical signal responsive thereto;

a signal processor coupled to said photo-detector to process said raw electrical signal to provide one or more processed output signals indicative of vital signs of the patient; and an output system that communicates said one or more output signals.

25. The fiber optic monitor of claim 24 wherein said casing is at least one cuff that is adapted to extend around a body part of said patient selected from the group consisting of an arm, a leg, a wrist, an ankle, a finger and combinations thereof.

26. The fiber optic monitor of claim 24 wherein said casing is a cuff that comprises a fabric body and a hook and loop fastener connected to said fabric body for fastening said cuff to said patient.

27. The fiber optic monitor of claim 24 comprising periodically calibrating said fiber optic monitor with a standard blood pressure measurement.

28. The fiber optic monitor of claim 24 comprising periodically calibrating said fiber optic monitor with a standard blood pressure measurement obtained from a sphygmomanometer.

29. The fiber optic monitor of claim 24 comprising means for periodically calibrating said fiber optic monitor with a standard blood pressure measurement by either manually or automatically periodically storing the standard measurement in a processor, and means for using said stored measurement to automatically adjust the calibration of said processed output signals from said fiber optic monitor corresponding to a blood pressure reading.

30. A fiber optic monitor for detecting vital signs in a patient, comprising:

optical fiber comprising a first optical path and a second optical path, said optical fiber being adapted to be situated proximate to a patient so that acousto-mechanical signals generated by said patient are coupled into said optical fiber effective to modulate a physical parameter of said optical fiber responsive to said acousto-mechanical signals;

an optical source coupled to supply optical radiation into an input of said first optical path and an input of said second optical path;

an optical system for creating interference from the optical radiation emitted from an output of said first optical path and an output of said second optical path;

a photo-detector arranged to sense an optical signal provided by time variations in said interference, said photo-detector providing a raw electrical signal responsive thereto;

a signal processor coupled to said photo-detector to process said raw electrical signal to provide one or more processed output signals indicative of vital signs of the patient; and an output system that communicates said one or more output signals.

31. The fiber optic monitor of claim 30 wherein said fiber optic monitor comprises a Sagnac interferometer configuration.

32. The fiber optic monitor of claim 30 wherein said fiber optic monitor comprises a Mach-Zehnder interferometer configuration.

33. The fiber optic monitor of claim 30 wherein said fiber optic monitor comprises a Fabry-Perot interferometer configuration.

34. The fiber optic monitor of claim 30 comprising a first reflector at a first end of a single said optical fiber and a second reflector spaced from said first reflector at a second end of said single optical fiber, said first reflector and said second reflector being disposed in said first optical path and said second optical path of said single optical fiber and said photodetector and said optical source being disposed at said first end of said single optical fiber.

35. The fiber optic monitor of claim 30 comprising a first reflector at a first end of a single said optical fiber and a second reflector spaced from said first reflector at a second end of said single optical fiber, said first reflector and said second reflector being disposed in said first optical path and said second optical path of said single optical fiber and said photodetector and said optical source being disposed at said first end of said single optical fiber, wherein said first reflector comprises a Fiber Bragg Grating.

36. The fiber optic monitor of claim 30 comprising a first reflector at a first end of a single said optical fiber and a second reflector spaced from said first reflector at a second end of said single optical fiber, said first reflector and said second reflector being disposed in said first optical path and said second optical path of said single optical fiber and said photodetector and said optical source being disposed at said first end of said single optical fiber, wherein said first reflector comprises a Fiber Bragg Grating and said second reflector comprises one of a Faraday Rotation Mirror and a Fiber Bragg Grating.

37. The fiber optic monitor of claim 30 wherein said fiber optic monitor comprises a Michelson interferometer configuration.

38. A method of detecting vital functions of a patient, comprising:

providing optical fiber comprising a first optical path and a second optical path, said optical fiber being proximate to a patient located in an area selected from the group consisting of an operating room, a recovery room, an intensive care unit, a magnetic resonance imaging laboratory, a computerized tomography scan laboratory, an elderly care facility and combinations thereof;

coupling optical radiation into an input of said first optical path and an input of said second optical path;

coupling acousto-mechanical signals indicative of vital signs generated by said patient into said optical fiber to modulate a physical parameter of said optical fiber responsive to said acousto-mechanical signals;

creating interference of optical radiation emitted from an output of said first optical path and an output of said second optical path;

detecting time variations of said interference and providing a time-varying electrical signal responsive thereto; and signal processing said time-varying electrical signal to provide one or more output signals indicative of said vital signs.

39. The method of claim 38 comprising communicating said output signals in a manner selected from the group consisting of: 1) as a local numerical or graphical readout near the patient, 2) over at least one of fiber optic lines, phone lines, power lines, local area network lines, and TV cable lines to produce a numerical or graphical readout at a central monitoring station, and the combination of 1) and 2).

40. The method of claim 38 further comprising measuring said vital signs using a technique selected from the group consisting of electrocardiogram, electroencephalogram, pulse oximetry, respiration measurement using capnograph or end-tidal volume $CO_2$, blood pressure measurement, body temperature measurement, and combinations thereof.

41. The method of claim 38 comprising containing at least a portion of said optical fiber with a casing comprising one of a cuff and a patch and affixing said casing to the body of said patient.

42. The method of claim 38 wherein said vital signs include at least one of blood pressure, heart rate and respiration.

43. The method of claim 38 wherein said vital signs include at least one of blood pressure, heart rate and respiration, comprising communicating an alarm under conditions selected from the group consisting of:

1) breath rate is faster or slower than a preset threshold value of the breath rate, 2) heart rate is faster or slower than a preset threshold value of the heart rate, 3) blood pressure is higher or lower than a preset threshold value of the blood pressure.

44. A method of detecting blood pressure of a patient, comprising:

providing optical fiber comprising a first optical path and a second optical path, said optical fiber being contained by a cuff;

wrapping said cuff around a body part of the patient;

applying pressure to said cuff effective to cause said optical fiber to contact the body part;

coupling optical radiation into an input of said first optical path and an input of said second optical path;

coupling acousto-mechanical signals indicative of blood pressure generated by said patient into said optical fiber to modulate a physical parameter of said optical fiber responsive to said acousto-mechanical signals;

creating interference of optical radiation emitted from an output of said first optical path and an output of said second optical path;

detecting time variations of said interference and providing a time-varying electrical signal responsive thereto; and signal processing said time-varying electrical signal to provide one or more output signals indicative of said blood pressure.

45. The method of claim 44 further comprising coupling acousto-mechanical signals indicative of heart rate generated by said patient into said optical fiber to modulate a physical parameter of said optical fiber responsive to said acousto-mechanical signals; wherein said signal processing of said time-varying electrical signal provides one or more output signals indicative of said heart rate, while providing said output signals indicative of said blood pressure.

* * * * *